(12) United States Patent
Shibata et al.

(10) Patent No.: US 10,927,363 B2
(45) Date of Patent: Feb. 23, 2021

(54) DNA SEQUENCE AND EXPRESSION VECTOR FOR ALGINATE LYASE

(71) Applicant: MIE UNIVERSITY, Tsu (JP)

(72) Inventors: Toshiyuki Shibata, Tsu (JP); Hideo Miyake, Tsu (JP); Yoshihiro Murase, Tsu (JP); Reiji Tanaka, Tsu (JP); Tetsushi Mori, Tokyo (JP); Haruko Takeyama, Tokyo (JP); Mami Takahashi, Tokyo (JP)

(73) Assignee: MIE UNIVERSITY, Tsu (JP)

( * ) Notice: Subject to any disclaimer, the term of this patent is extended or adjusted under 35 U.S.C. 154(b) by 0 days.

(21) Appl. No.: 16/090,994

(22) PCT Filed: Apr. 3, 2017

(86) PCT No.: PCT/JP2017/013871
§ 371 (c)(1),
(2) Date: Oct. 3, 2018

(87) PCT Pub. No.: WO2017/175694
PCT Pub. Date: Oct. 12, 2017

(65) Prior Publication Data
US 2019/0127722 A1 May 2, 2019

(30) Foreign Application Priority Data

Apr. 4, 2016 (JP) .................................. 2016-075364

(51) Int. Cl.
| | |
|---|---|
| *C12N 9/88* | (2006.01) |
| *C12P 19/02* | (2006.01) |
| *G01N 30/88* | (2006.01) |
| *G01N 30/26* | (2006.01) |
| *G01N 30/02* | (2006.01) |
| *G01N 30/72* | (2006.01) |

(52) U.S. Cl.
CPC .............. *C12N 9/88* (2013.01); *C12P 19/02* (2013.01); *C12Y 402/02* (2013.01); *G01N 30/02* (2013.01); *G01N 30/26* (2013.01); *G01N 30/7233* (2013.01); *G01N 30/88* (2013.01); *G01N 30/72* (2013.01); *G01N 2030/027* (2013.01); *G01N 2030/8831* (2013.01)

(58) Field of Classification Search
None
See application file for complete search history.

(56) References Cited

U.S. PATENT DOCUMENTS

| | | |
|---|---|---|
| 2014/0017798 A1 | 1/2014 | Yu |
| 2014/0106414 A1 | 4/2014 | Kambourakis et al. |
| 2014/0206047 A1 | 7/2014 | Kambourakis et al. |
| 2014/0315318 A1 | 10/2014 | Lu et al. |
| 2015/0027206 A1 | 1/2015 | Lu |

FOREIGN PATENT DOCUMENTS

| | | |
|---|---|---|
| JP | 2012210208 A | 11/2012 |
| JP | 2012235773 A | 12/2012 |
| JP | 2015536641 A | 12/2015 |
| WO | 2013128285 A2 | 9/2013 |
| WO | 2014047510 A1 | 3/2014 |
| WO | 2015143381 A2 | 9/2015 |
| WO | 2015074025 A9 | 12/2015 |

OTHER PUBLICATIONS

Mod et al. Genome Announc. Jul.-Aug. 2014; 2(4): e00826-14 (Year: 2014).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Sambrook et al. Molecular cloning a Laboratory Manual, 2nd edition, Cold Spring Harbor, N.Y. 1989, pp. 8.46-8.52 and pp. 11.2-11.19 (Year: 1989).*
Li et al. J Biochem. Jan. 2016;159(1):77-86. Epub Jul. 30, 2015 (Year: 2015).*
Nishi, S., et al., alginate lyase precursor [Loktanella cinnabarina LL-001], Database DDBJ/EMBL/GenBank [online], Accession No. GAD57170, Sep. 16, 2015 uploaded, [retrieved on May 12, 2017].
Nishi, S., et al., oligo alginate lyase [Loktanella cinnabarina LL-001], Database DDBJ/EMBL/GenBank [online], Accession No. GAD57174, Sep. 16, 2015 uploaded, [retrieved on May 12, 2017].
English translation of the International Search Report dated Jun. 27, 2017 for parent application No. PCT/JP2017/013871.
English translation of the Written Opinion of the International Searching Authority for parent application No. PCT/JP2017/013871.
Mori, Tetsushi, et al. "Highly efficient alginate lyases from *Falsirhodobacter* p. alg1"—Abstracts of Lectures of The Society for Biotechnology Japan, vol. 67, p. 97 (1P-036) Sep. 25, 2015.
Mori, Tetsushi, et al. "Screening for exolytic alginate lyases from marine bacteria"—Abstracts of Lectures of The Society for Biotechnology Japan, vol. 65, p. 59 (1P-166) Aug. 25, 2013.
Takahashi, Mami, et al, "Search for alginate lyases from brown-decomposing bacteria and evaluation of resolution"—Abstracts of the Marine Biotechnology Conference of Japanese Society for Marine Biotechnology, vol. 16, p. 53, May 31, 2015.

(Continued)

*Primary Examiner* — Christian L Fronda

(74) *Attorney, Agent, or Firm* — J-Tek Law PLLC; Jeffrey D. Tekanic; Scott T. Wakeman

(57) ABSTRACT

Alginate lyase activity is exhibited by the amino acid sequences (polypeptides) shown in SEQ ID No:1 and SEQ ID No:2. These polypeptides and their homology equivalents are used to produce 4-deoxy-L-erythro-5-hexoseulose uronic acid (DEH) by contacting the polypeptide(s) with an alginate containing a uronic acid moiety and holding the mixture of the alginate and the polypeptide(s) at a temperature at which alginate lyase activity is exhibited.

10 Claims, 12 Drawing Sheets

Specification includes a Sequence Listing.

(56) References Cited

OTHER PUBLICATIONS

Takahashi, Mami, et al., "Characterization of alginate lyase AlyFRB obtained from brown algae *Falsirhodobacter* sp. alg1"—Abstracts of the Marine Biotechnology Conference of Japanese Society for Marine Biotechnology, vol. 17, pp. 68 (0-1-5) May 30, 2015.

Wang, D.M., et al., "Optimal production of 4-deoxy-L-erythro-5-hexoseulose uronic acid from alginate for brown macro algae saccharification by combining endo- and exo-type alginate lyases", 2014, Bioprocess and Biosystems Engineering, vol. 37, p. 2105-2111.

T Mori, et al, *Falsirhodobacter* sp. alg1 gene for 16S ribosomal RNA, partial sequence, Mar. 13, 2014.

T Mori, et al., *Falsirhodobacter* sp. alg1 Harbors Single Homologs of Endo and Exo-Type Alginate Lyases Efficient for Alginate Depolymerization, PLOS ONE | DOI:10.1371/journal.pone.0155537 May 13, 2016.

T Mori, et al, *Falsirhodobacter* sp. alg1 alyFRA gene for endo-type alginate lyase, complete cds, May 26, 2016.

T Mori, et al, *Falsirhodobacter* sp. alg1 alyFRB gene for oligoalginate lyase, complete cds, May 26, 2016.

PET-22b(+) Vector, Novagen, created Dec. 10, 1998.

\* cited by examiner

DNA SEQUENCE AND EXPRESSION VECTOR FOR ALGINATE LYASE

CROSS-REFERENCE

This application is the US national stage of International Patent Application No. PCT/JP2017/013871 filed on Apr. 3, 2017, which claims priority to Japanese Patent Application No. 2016-075364 filed on Apr. 4, 2016.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| MIE008_SEQUENCE_LISTING_2.txt | Nov. 17, 2020 | 20 |

TECHNICAL FIELD

The invention relates to DNA sequences and expression vectors for alginate lyases.

BACKGROUND ART

Aquatic plants in the world are produced 7 million tons per year, of which brown algae occupy 68.6% of them, and alginic acid is the most abundant and accounts for 30% among its constituent polysaccharides. Some brown algae containing kelp and seaweed are used as food, but most are unused resources. Since brown algae do not require cultivation field, fresh water and fertilizers, they are essentially in a gel state, so it is pointed out that it is easier to cause enzymatic reaction than terrestrial biomass. Especially, Japan is surrounded by the sea, and has larger marine area than other countries in the world. If brown algae can be used, it can be a stable raw material supply source. Further, since alginic acid is the most constituent polysaccharide of brown algae, the use of alginic acid becomes important.

Alginate is a linear polymer in which two types of uronic acids, beta-D-mannuronic acid and alpha-L-guluronic acid, which is C5 epimer of beta-D-mannuronic acid, are bonded via a glycoside bond (FIG. 1). In alginate, three types of blocks, which are poly(M) block in which beta-D-mannuronic acids are bound, poly(G) block in which alpha-L-guluronic acids are bound, and poly(M G) block in which beta-D-mannuronic acid and alpha-L-guluronic acid are alternately bound, exist with mixed condition.

Thus far, several microorganisms which can metabolize alginate have been found, and they have alginate lyases. Alginate lyase belongs to polysaccharide lyases (PLs) that cleave glycosidic bond by beta-elimination. Currently, alginate lyases are divided into PL5, PL6, PL7, PL14, PL15, PL17, and PL18 family. Two types of cutting manners are known; one is endo-type that degrades polymer to saturated oligosaccharide and unsaturated oligosaccharide, the other is exo-type that degrades polymer to saturated monosaccharide or unsaturated monosaccharide. Currently, PL5 and PL7 belong to endo-type, PL15 and PL17 belongs to exo-type. Unsaturated monosaccharide that is produced in degradation by exo-type alginate lyase and the unsaturated double bond of the pyranose ring is opened by the non-enzymatic reaction, to become 4-deoxy-L-erythro-5-hexoseulose uronic acid (DEH). Some marine microorganisms and metabolically modified fermenting microorganisms can utilize DEH, and make organic acids such as lactic acid and succinic acid, biofuels such as bioethanol. Therefore, methods for producing DEH efficiently have been studied (Patent document 1 and 2, Non-patent document 1 to 5).

PRIOR ART LITERATURE

Patent Documents

Patent document 1: JP2012-235773 A
Patent document 2: JP2012-210208 A

Non-Patent Documents

Non-patent document 1: Bioprocess Biosyst Eng, Vol. 37, No. 10, Page 2105-2111 (2014.10)
Non-patent document 2: Abstracts of Lectures of The Society for Biotechnology Japan, Vol. 67, Page 97 (2015.09.25)
Non-patent document 3: Abstracts of the Marine Biotechnology Conference of Japanese Society for Marine Biotechnology, Vol. 17, Page 68 (2015.05.30)
Non-patent document 4: Abstracts of the Marine Biotechnology Conference of Japanese Society for Marine Biotechnology, Vol. 16, Page 53 (2015.05.31)
Non-patent document 5: Abstracts of Lectures of The Society for Biotechnology Japan, Vol. 65, Page 59 (2013.08.25)
Non-patent document 6: Da Mao Wang, Hee Tamek Kim, Eun Ju Yun Do Hyoung Kim, Yong-Cheol Park, Hee Chul Woo, Kyoung Heon Kim (2014) Optimal production of 4-deoxy-L-erythro-5-hexoseulose uronic acid from alginate for brown macro algae saccharification by combining endo- and exo-type alginate lyases. Bioprocess Biosyst Eng 37, 2105-2111.

SUMMARY OF THE INVENTION

It is one non-limiting object of the present teachings to disclose DNA sequences and expression vectors for preparing an alginate lyase capable of producing uronic acid monosaccharide at an industrial level.

In the invention for solving the above-mentioned problems, a polypeptide is provided which has the amino acid sequence shown in SEQ ID NO:1 (MSTENKSRSNLFPLDEPKAGRLTIQYGPLETTTLIEN-PPRFSWLPVIEDGA TYALRISTDPEYSAANTLLF-SGIQLNFFTPDAPLAAGTWYWSYAQCDASGK PVTEWSTSRRITLDEGLPQTPLAPRKTRFDAATRAH-PRLWMDGGRLEQFR KDVAADPTHCTW-STFFEGSVLPWMDRDIIEEPVGYPDHKRVAK-IWRKVYI ECQELMYAIRHLAVGGQVTQDAAMLARAKEWLL-SAARWNPAGTTSRAYT DEWAFRVNLA-LAWGYDWLYDQLDEDERTLVRTALLER-TRQTADHLMRH ASIHLFPFDSHAVRAVSAVLIPACIALLDDEPEAE-DWLNYAVEFLFTVYSP WGDHDGGWAEG-PHYWMTGMAYLIDAANLLRGWSGID-LYQRPFFQKTGD FPLYTKAPDTRRATFGDDSTMGDLPAIKVGYNLRQY- AGVTGNGAYQWYY DEILRTNPGTEMA-
FYNWGWWDFRFDEMLYRTDFPIVEAVPPADED-
ALRW
FKGIGWVAIQHRMQAPDEHVQFVFKSSPYG-
SISHSHGDQNAFCLSAFGED LAIQSGHYVAFN-
STMHQNWRRQTLSKNAILIDGKGQY-
AGKDKAIAMQSTG
KVNIAEDRGDHIFLQGDATEAYRTLSPE-
VRSVVRDVYFVNREYFVIVDAID ADTPVSIDWRL-
HANAPFNLGDSSFRYTGEKAGFYGQILWSEAGPAEL-
TQE
TGFPDVDPSEIEGLPVSTCLTARFPKSTRHRIATLIVPY-
ALDAPRRIFSFLDD QGYDCD-
LYFTDANDNSFRVIVPKTFDVGTPGIKNN), or which
has an amino acid sequence having homology of at least
90% or more with the sequence and exhibits exo-type
alginate lyase activity.

The DNA encoding the polypeptide can also be provided.
An expression vector having the DNA in a state capable of
expressing the polypeptide can be provided.

In another invention, a production system of 4-deoxy-L-
erythro-5-hexoseulose uronic acid (DEH) comprising the
steps of: (a) an enzyme addition step of contacting the
polypeptide with alginate containing uronic acid moiety, and
(b) an enzyme action step of holding the mixture of the
alginate and the polypeptide at a temperature at which the
exo-type alginate lyase acts is provided. A method that
includes the steps of (a) and (b) can produce DEH.

In another invention, a polypeptide is provided which has
the amino acid sequence shown in SEQ ID NO:2
(MSLKLRTFCLAGTATIFVALPSTYA-
LAAGTGACTGVSQLAIVSASDDGTFD DIYAPEFAID-
GEFGPSSRWSSLGEGKQLVLDLGEPQTV-
SEVGLAWYKGNE
RTSSFTLEASNDGENWMPLMDRTE-
SAGKSEAVEKYSFDATEARYVRVTG MGNSASGWNS-
LYEAQVFGCGSGEIAATGDGSGEVKEAD-
VSAYGLRTDVPP
SENFDLTHWKLTLPADRDNDGKV-
DEIEEEELQGWSDPRFFYTDPATGGM VFRTAP-
DGKTTSGSHYTRSELREMIRGGDKSI-
ATRVDDGTPNKNNWVFST
APEEAQALAGGVDGTMTATLAVNHVTRTGESGKI-
GRVIIGQIHAMDDEPIR LYYRKLPTNKYGSIYFAHEP-
VGGDDDLVNVIGDRGSDIDNPADGIALDEVF
SYEIKVTSEEKDGELHPILNVSITRDDGTVVKAE-
PYDMFESGYSTDKDFMY FKAGAYSQNNSIT-
WPDDFDQVTFYALDVTHGE), or which has an amino
acid sequence having homology of at least 90% or more with
the sequence and exhibits endo-type alginate lyase activity.

Further, the DNA encoding the polypeptide is provided.
An expression vector having the DNA in a state capable of
expressing the polypeptide can be provided.

Further, a production system of DEH comprising the steps
of (c) a plural-enzymes addition step of contacting two kinds
of polypeptides of the polypeptide which has the amino acid
sequence shown in SEQ ID NO:1 or which has an amino
acid sequence having homology of at least 90% or more with
that of SEQ ID NO:1 and has exo-type alginate lyase
activity, and a polypeptide having endo-type alginate lyase
activity with alginate containing uronic acid moiety, and (d)
a plural-enzymes action step of holding the mixture of the
alginate and two polypeptides at a temperature at which the
alginate lyases act is provided. A method that includes the
steps of (c) and (d) can produce DEH.

At this time, any polypeptide having endo-type alginate
lyase activity can be used, but endo-type alginate lyase
which has the amino acid sequence shown in SEQ ID No:2
or which has an amino acid sequence having homology of at
least 90% or more with the amino acid sequence preferably
can be used.

Polypeptides according to the invention are polypeptides
containing the amino acid sequences shown in SEQ ID No:
1 and SEQ ID No: 2 or those having homology of at least
90% or more with the sequence of SEQ ID No: 1 and SEQ
ID No: 2. Moreover, polypeptides for use in the method for
producing unsaturated uronic acid monosaccharide accord-
ing to the invention are those containing the amino acid
sequences shown in SEQ ID No: 1 and/or SEQ ID No: 2 or
those having homology of at least 90% or more with the
sequence of SEQ ID NO: 1 and/or SEQ ID NO: 2.

The homology of amino acid sequence is at least 90%,
91%, 92%, 93%, 94%, more preferably 95%, 96%, 97%,
98% or 99%, or 100% identical.

A polypeptide which has the amino acid sequence shown
in SEQ ID NO; 1 or SEQ ID NO:2 or which has an amino
acid sequence having homology of at least 90% or more with
that of SEQ ID NO: 1 or SEQ ID NO: 2 naturally exhibits
alginate lyase activity.

The polypeptide having the amino acid sequence shown
in SEQ ID NO: 1 is a novel enzyme having exo-type alginate
lyase activity (Exo.Al.Ly). The amino acid sequence shows
only 40% or less homology compared to that of known
exo-type alginate lyases. Furthermore, the enzymatic activ-
ity is sufficiently strong, compared to that of known
enzymes.

A polypeptide having an amino acid sequence having
homology of at least 90% or more with that of SEQ ID NO:
1 has 30% or more, preferably 50% or more, 70% or more
of exo-type alginate lyase activity compared to the polypep-
tide shown in SEQ ID NO: 1.

DNA encoding a polypeptide having an amino acid
sequence means DNA that encodes the amino acid sequence
having that shown in SEQ ID NO: 1 or DNA that encodes
an amino acid sequence with homology of at least 90% or
more compared to SEQ ID NO: 1 of which the polypeptide
has exo-type alginate lyase. Three consecutive bases of
DNA encode an amino acid, plural codes may encode the
same amino acid. As long as the DNA sequences encode the
polypeptide, an appropriate sequence can be designated with
reference to the genetic code. However, an appropriate DNA
sequence can be preferably used depending on the stability
and expression vector of an expression system. When using
a vector that expresses in *E. coli*, the DNA sequence as
shown in SEQ ID NO: 3 can be used for encoding the amino
acid sequence of SEQ ID NO: 1.

The polypeptide having the amino acid sequence shown
in SEQ ID NO: 2 is a novel enzyme exhibiting endo-alginate
lyase activity (Endo.Al.Ly). The amino acid sequence shows
only 40% or less homology compared to that of known
endo-alginate lyases. Furthermore, the enzymatic activity is
sufficiently strong, compared to that of known enzymes.

A polypeptide having an amino acid sequence having
homology of at least 90% or more with that of SEQ ID NO:
2 has 30% or more, preferably 50% or more, 70% or more
of endo-type alginate lyase activity compared to the poly-
peptide shown in SEQ ID No: 2.

DNA encoding a polypeptide having the amino acid
sequence means DNA that encodes the amino acid sequence
having that shown in SEQ ID NO: 2 or DNA that encodes
an amino acid sequence with homology of at least 90% or
more compared to SEQ ID NO: 2 of which the polypeptide
has endo-type alginate lyase. As long as the DNA sequences
encode the polypeptide, an appropriate sequence can be designated with reference to the genetic code. When using a vector that expresses in *E. coli*, the DNA sequence as shown in SEQ ID NO: 4 can be used for encoding the amino acid sequence of SEQ ID NO: 2.

In the invention, the term "isolated" polypeptide means a polypeptide which is separated and purified to the extent where it does not exist in nature, and which exhibits the alginate lyase activity. It does not mean that there are no impurities at all.

In the invention, the term "alginate" means starting materials for producing unsaturated uronic acid monosaccharide, it contains alginate from brown algae, and partially degraded alginate by alginate lyase (e.g., oligosaccharide).

In the invention, the term "unsaturated uronic acid monosaccharide" means unsaturated monosaccharides having a double bond at the non-reducing end that is liberated from alginate or the end of alginate oligosaccharide by a beta-elimination reaction of exo-type alginate lyase.

In the invention, the term "uronic acid moiety" means M or G linked by a beta-1-4 linkage in alginate.

In the invention, the term "contacting" a polypeptide or two kinds of polypeptides with alginate means to mix two materials in a solid state, an aqueous solution or a suspension under the condition that the alginate lyase activity of the polypeptide acts. One or two kinds of polypeptides and alginate may be a different form before mixing.

In the invention, the "temperature at which alginate lyase acts" means the temperature at which the enzyme can act for a predetermined period (e.g., 72 hours or less, preferably 24 hours or less, more preferably less than 3 hours) without losing the alginate lyase activity. The temperature conditions can be determined appropriately, depending on other reaction conditions (e.g., including conditions such as alginate concentration, polypeptide concentration, the type of aqueous solution (water containing no components other than alginate and polypeptide, such as an aqueous solution containing a suitable salt)).

When contacting two kinds of polypeptides (endo-alginate lyase or exo-type alginate lyase) with alginate, two polypeptides can be contacted simultaneously, or one by one can be sequentially contacted.

According to another invention, a LC-MS (liquid chromatograph mass spectrometer) apparatus for measuring DEH that comprises a column for anion analysis, and an HPLC (high performance liquid chromatograph) having ammonium formate buffer containing formic acid solution as a mobile phase is provided. In the invention, a method for measuring DEH by LC-MS (liquid chromatograph mass spectrometer) which has an HPLC (high performance liquid chromatography) that has a column for anion analysis having ammonium formate buffer containing formic acid buffer as a mobile phase is provided.

According to the components above, by using ammonium formate buffer containing formic acid as a mobile phase of HPLC, DEH can be analyzed without gradient solvent delivery. Therefore, many samples can be measured quickly, since the time for measurement per sample is shortened, compared to a method using gradient solvent delivery.

Commercially available columns can be used for anion analysis. However, Shodex IC NI-424 or I-524A preferably can be used.

According to the invention, a polypeptide shown in SEQ. ID. NO. 1 exhibiting exo-type alginate lyase activity, a polypeptide shown in SEQ. ID. NO. 2 exhibiting endo-type alginate lyase activity, and a method for producing unsaturated uronic acid monosaccharide using these polypeptides can be provided.

DETAILED DESCRIPTION

Figure 1:
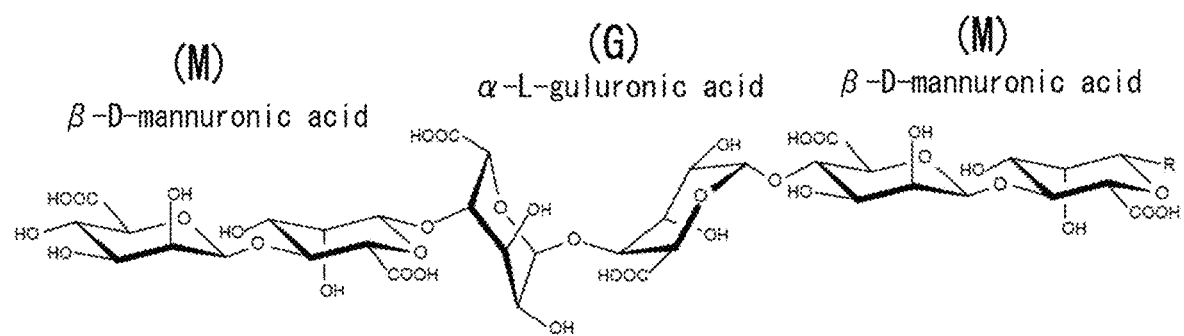
FIG. 1 shows the chemical structure of alginate.

Next, embodiments of the invention will be explained in detail with reference to the figures. The technical scope of the invention is not limited by these examples and can be carried out in various forms without changing the gist of the invention.

<Preparation of Recombinants for Expressing Exo.Al.Ly and Endo.Al.Ly, Expression of Exo.Al.Ly and Endo.Al.LY, and Purification Thereof>

To produce DEH from alginate by an enzymatic reaction using two enzyme proteins, which are the Endo-type alginate lyase (Exo.Al.Ly) and the exo-type alginate lyase (Endo.Al.Ly), two plasmids for protein expression were constructed using an *E. coli* expression vector, and enzyme proteins were expressed, solubilized, and purified until they became a single band. As the DNA encoding Exo.Al.Ly, SEQ. ID. No. 3 was used (ATGTCGACGGAAAACAAATCCCGTTCAAACCTGTTTCCACTTGATGAGCC CAAAGCGGGACGGCTGACGATCCAATATGGCCCGCTCGAAACGACGACG CTGATTGAAAACCCGCCACGCTTCTCATGGCTGCCGGTCATCGAGGATGG CGCAACCTATGCGCTGCGCATCTCGACCGATCCCGAATATTCCGCGGCAA ACACCCTCCTGTTTTCGGGCATCCAGCTGAACTTCTTCACGCCTGATGCA CCTTTGGCGGCAGGCACTTGGTACTGGTCCTATGCACAATGCGATGCCTC GGGAAAGCCCGTTACCGAATGGAGCACGAGCCGTCGCATCACTCTCGAC GAGGGTCTGCCACAGACACCGCTGGCACCACGCAAGACGCGTTTTGACG CGGCGACCCGTGCGCACCCGCGCCTGTGGATGGACGGCGGCCGGCTGGA ACAGTTCCGCAAGGATGTTGCCGCCGACCCGACGCATTGCACATGGTCTA CCTTTTTCGAGGGTTCGGTTCTGCCGTGGATGGACCGCGACATCATCGAA GAGCCTGTGGGCTATCCGGATCACAAGCGTGTCGCGAAGATCTGGCGCAA GGTCTACATCGAGTGTCAGGAACTGATGTATGCGATCCGCCACCTTGCTG TGGGCGGTCAGGTTACCCAGGACGCGGCAATGCTGGCACGCGCCAAGGA ATGGCTGCTCAGCGCCGCACGCTGGAATCCGGCAGGCACCACCTCGCGC GCCTATACCGATGAATGGGCTTTCCGTGTGAACCTCGCACTCGCATGGGG TTATGACTGGCTCTATGACCAGCTGGACGAGGATGAGCGTACGCTGGTCC GCACCGCCTTGCTGGAGCGTACGCGCCAGACGGCGGATCACCTGATGCG CCACGCCAGCATCCACCTGTTTCCGTTTGACAGCCACGCTGTCCGCGCGG TGTCTGCGGTTCTGATCCCCGCCTGTATTGCCTTGCTGGATGATGAACCC GAGGCCGAGGACTGGCTGAACTATGCGGTGGAATTCCTGTTCACCGTCTA TTCGCCGTGGGGCGATCATGACGGTGGCTGGGCCGAGGGTCCGCACTAC TGGATGACGGGTATGGCCTATCTGATCGACGCGGCAAACCTGCTGCGCGG CTGGAGCGGAATCGACCTGTACCAACGCCCGTTCTTCCAGAAAACCGGGG ACTTCCCGCTTTATACCAAGGCGCCGGACACACGTCGGGCCACATTCGGC GATGATAGCACCATGGGCGATCTGCCCGCGATCAAGGTCGGATATAACCT GCGTCAATACGCAGGGGTGACCGGCAACGGTGCCTACCAATGGTACTACG ACGAAATCCTGCGCACCAACCCCGGCACGGAAATGGCCTTCTACAACTGG GGCTGGTGGGATTTCCGGTTTGACGAAATGCTCTACCGCACGGACTTCCC GATCGTAGAGGCAGTTCCGCCCGCGGATGAGGATGCACTGCGCTGGTTCA AGGGCATCGGTTGGGTCGCGATCCAGCACCGTATGCAGGCACCGGACGA GCATGTTCAATTCGTGTTCAAATCCTCTCCCTACGGCTCGATCAGCCACAG CCATGGGGATCAGAACGCGTTCTGTCTGTCGGCATTCGGTGAGGATCTTG CAATCCAGTCCGGCCATTATGTCGCCTTCAACTCGACAATGCACCAGAAC TGGCGTCGCCAGACCCTGTCGAAGAACGCCATCCTGATCGACGGAAAAG GCCAGTACGCCGGCAAGGACAAGGCGATTGCCATGCAATCGACCGGTAA GGTCAATATTGCCGAGGATCGTGGCGATCATATCTTCCTGCAGGGGGATG CGACCGAAGCCTATCGCACATTGTCACCCGAGGTCCGCTCGGTTGTCCGT GATGTGTATTTCGTGAATCGCGAATATTTCGTGATCGTGGATGCCATCGAT GCGGATACGCCCGTCAGCATCGACTGGCGTCTGCACGCGAATGCTCCGTT CAATCTGGGTGATAGCAGCTTCCGCTATACCGGTGAAAAGGCCGGTTTCT ATGGCCAGATCCTGTGGTCCGAGGCGGGTCCTGCCGAACTGACGCAGGA AACCGGCTTTCCGGATGTCGATCCGAGCGAAATCGAGGGACTGCCGGTCA GCACCTGCCTGACCGCCCGTTTCCCCAAATCCACCCGTCATCGTATCGCG ACCTTGATCGTCCCGTATGCTCTGGATGCGCCGCGCCGCATTTTCAGCTT CCTTGATGATCAGGGTTACGACTGCGATCTCTATTTCACCGATGCCAATGA CAATAGTTTCAGGGTGATTGTTCCCAAGACGTTCGACGTGGGAACACCTG GCATCAAAAATAACTGA); as the DNA encoding Endo-.Al.Ly, SEQ. ID. No. 4 was used (ATGAGTCTGAAGCTACGCACGTTCTGTTTGGCAGGTACGGCGACTATTTT TGTCGCATTACCATCAACCTATGCATTGGCAGCCGGAACCGGCGCATGCA CCGGGGTGTCCCAGCTGGCCATTGTATCGGCCAGCGATGACGGCACTTTC GATGACATCTACGCACCTGAATTCGCGATCGACGGCGAATTCGGCCCAAG TTCGCGCTGGTCATCCCTTGGGGAGGGGAAGCAGCTTGTTCTGGATCTGG GAGAGCCCCAGACCGTAAGCGAGGTTGGTCTGGCCTGGTACAAGGGCAA TGAGCGCACATCCAGCTTTACGCTGGAAGCTTCGAATGACGGCGAAAACT GGATGCCTTTGATGGACCGCACGGAAAGTGCCGGAAAATCCGAGGCTGT GGAGAAATACAGCTTTGACGCGACCGAGGCCCGCTATGTTCGGGTGACCG GTATGGGCAATAGCGCGAGCGGCTGGAACAGCCTTTACGAGGCACAGGT GTTCGGCTGTGGCTCAGGTGAGATTGCGGCCACAGGCGACGGTTCCGGA GAGGTCAAGGAAGCAGACGTCAGCGCCTATGGCCTGCGTACCGACGTTC CGCCAAGCGAGAACTTCGATCTGACCCACTGGAAGCTGACATTGCCGGCG GATCGGGACAATGACGGCAAAGTGGACGAGATTGAGGAAGAAGAGCTGC AGGGTTGGTCTGATCCCCGGTTCTTCTATACCGATCCGGCAACGGGTGGC ATGGTTTTCCGCACCGCTCCGGATGGAAAGACCACCTCGGGATCGCATTA TACGCGCAGCGAACTGCGCGAGAT GATCCGCGGCGGTGACAAGAGCATT GCCACGCGCGTGGATGACGGAACGCC-CAACAAGAACAACTGGGTGTTCT CGACGGCGCCCGAAGAGGCGCAGGCCCTTGCCG-GCGGGGTGGACGGGA CCATGACGGC-CACGTTGGCGGTGAACCATGTGACCCGTACCG-GAGAATCC GGCAAGATCGGGCGTGTCAT-CATCGGCCAGATCCACGCGATGGATGACGA GCCTATCCGGCTTTATTATCGCAAGCTTCCGAC-CAATAAATACGGCTCCAT CTATTTCGCGCAT-GAGCCGGTAGGGGCGACGATGATCTGGT-CAACGTCA TCGGGGATCGTGGAAGCGATATTGACAACCCTGCG-GATGGCATCGCGCTG GACGAAGTGTTCTCT-TACGAGATCAAGGTGA-CATCCGAAGAAAAGGATGG AGAGCTGCATCCGATTCTGAATGTTTCCAT-CACGCGCGATGACGGAACGG TGGT-GAAAGCCGAACCCTACGA-CATGTTCGAAAGCGGGTATTCGACCGAC AAGGACTTCATGTACTTCAAGGCCGGAGCCTAT-TCGCAGAACAATTCCAT CACATGGCCGGACGAT-TTCGATCAGGTGACCTTCTACGCGCTGGATGTGA CGCACGGCGAATAA).

1. Method (1) Subcloning of Exo.Al.Ly Gene

A plasmid, in which Endo.Al.Ly was incorporated (It was named [Exo.Al.Ly gene plasmid].), given by a coworker was used to produce a protein expression system using *E. coli*. For the purification of the protein after expression smoothly, the stop codon of the gene encoding Endo.Al.Ly was deleted, and His-Tag was added at the C-terminal side. Primers to amplify the nucleotide sequence region of Exo.Al.Ly gene without the signal peptide and stop codon were designed. KOD-Plus-Neo (TOYOBO) as the DNA polymerase and Exo.Al.Ly gene plasmid as a template were used. By using the designed two primers (Exo.Al.Ly_Nde1_F: SEQ ID NO 5: tat cat tgC ATA TGa tgt cga cgg aaa aca aat ccc and Exo.Al.Ly_Xho1_R: SEQ ID NO 6: gca gCT CGA Ggt tat ttt tga tgc cag. Restriction enzyme's recognition sites were indicated in capital letters.), PCR was performed under the following conditions to amplify the target gene sequence.

As the PCR solution, 5 µL of 10×PCR buffer, 5 µL of 2 mM dNTPs, 3 µL of 25 mM MgSO$_4$, 1.5 µL of 10 µM Exo.Al.Ly_Nde1_F, 1.5 µL of 10 µM Exo.Al.Ly_Xho1_R, 1 µL of DNA template and 1 µL of DNA polymerase (KOD-Plus-Neo) were used, and dH$_2$O was added to a total volume of 50 µL. As the PCR conditions, after a 2 minute modification reaction at 94° C., as an amplification cycle containing (i) at 98° C. for 10 seconds for denaturation, (ii) at 60° C. for 30 seconds for annealing, and (iii) at 68° C. for 1 minute 20 seconds for synthesis were set, the amplification cycle containing (i) to (iii) was repeated 30 times.

After PCR was carried out, the amplified gene was fractionated by agarose gel electrophoresis and purified using the Wizard SV Gel and PCR Clean-up System (Promega).

(2) Construction of Exo.Al.Ly Construct

Exo.Al.Ly amplified by PCR and pET22b(+) (Novagen) were digested with Xho I and Nde I (TOYOBO). Then, targeted DNA was fractionated by agarose gel electrophoresis and purified using the Wizard SV Gel and PCR Clean-up System (Promega).

A ligation reaction mixture, in which the weight ratio of the purified insert gene and plasmid vector was contained at 3:1, was prepared, and ligation reaction was performed for 30 minutes at 16° C. with Ligation high Ver. 2 (TOYOBO). Then, the ligation product was transformed into *E. coli* DH5a, inoculated on LB agar medium containing 100 µg/mL ampicillin, and cultured overnight stationary at 37° C.

After culturing, colony PCR was performed in order to confirm that the target gene was inserted into the colonies generated on the LB agar medium. PCR was carried out using Quick-Taq as the polymerase (TOYOBO), Exo.Al.Ly_Nde1_F and Exo.Al.Ly_Xho1_R as the primers and the colony as the template.

As the PCR solution, 60 µL of Quick-Taq, 2.4 µL of 10 µM Exo.Al.Ly_Nde1_F and 2.4 µL of 10 µM Exo.Al.Ly_Xho1_R were used, and dH$_2$O was added to a total volume of 120 µL. As PCR conditions, after a 2 minute modification reaction at 94° C., as an amplification cycle containing (i) at 94° C. for 30 seconds for denaturation, (ii) at 60° C. for 30 seconds for annealing, and (iii) at 68° C. for 2 minutes 30 seconds for synthesis were set, the amplification cycle containing (i) to (iii) was repeated 25 times.

The PCR product was checked by agarose gel electrophoresis and the colony in which the target gene was inserted was selected. The selected colony was cultured with shaking at 37° C. in LB liquid medium overnight. Then, plasmid DNA was extracted using the Wizard Plus SV Minipreps DNA Purification System (Promega). The plasmid DNA was named pET22b(+)-Exo.Al.Ly.

(3) Confirmation of the Expression of Endo.Al.Ly and Exo.Al.Ly

The plasmid (pET25b(+)-Endo.Al.Ly plasmid) which encoded the polypeptide shown in SEQ ID NO.2 (Endo.Al.Ly) and can express Endo.Al.Ly using *E. coli* was obtained according to a similar procedure to above (1) and (2).

Thus, pET22b(+)-Exo.Al.Ly plasmid and pET25b(+)-Endo.Al.Ly plasmid was transformed into *E. coli* strain BL21 (DE3), respectively, planted on an LB agar medium containing 100 µg/mL of ampicillin and cultured overnight stationary at 37° C. Colonies on cultured LB agar medium were collected, inoculated into 5 mL of LB liquid medium containing 100 µg/mL of ampicillin and cultured at 37° C. with shaking at 160 rpm. After the turbidity of the culture solution became OD600=0.4-0.6, isopropyl-ß-thiogalactopyranoside (IPTG) was added to 0.1 mM and 1 mM, and cultured at 37° C. with shaking at 160 rpm. As a control, a colony was cultured without IPTG.

After culturing, 1 mL of each culture broth was centrifuged at 13000 rpm for 3 minutes, the supernatant was removed and the cells were suspended in 20 µL of 50 mM Tris-HCl buffer (ph7.5). 20 µL of 2×SDS sample buffer was added to the cell suspension, boiled for 3 minutes, and subjected to SDS-PAGE using 10% polyacrylamide gels to confirm the expression of the target protein.

(4) Large Scale Culture and Solubilization of the Enzyme Protein

Colonies of *E. coli* BL21(DE3) that grew on the LB agar medium were inoculated into 5 mL of LB liquid medium containing 100 µg/mL of ampicillin at 37° C. overnight with shaking, respectively, and were named pre-culture solution.

400 mL of 2×YT medium containing 100 µg/mL of ampicillin and 1% (w/v) of glucose at a final concentration was named main culture solution. 400 µL of the pre-culture solution was inoculated into the main culture solution, and incubated 37° C. with shaking at 160 rpm. After the turbidity of the culture solution became OD600=0.4-0.6, the main culture solution was cooled on ice for 10 minutes. Then, IPTG was added to a final concentration of 0.1 mM, and incubated at 20° C. for two nights with shaking.

After culturing, the culture solution was centrifuged at 4° C. at 6000 rpm for 25 minutes, and wet cells were obtained by removing the supernatant. 20 mM phosphate buffer containing 100 mM NaCl (pH7.4) was added to the wet cells at a proportion of 10 ml of buffer per 1 g of cells, and suspended. The suspension was sonicated (OUTPUT 4, DUTY 40: TOMMY ULTRASONIC DISRUPTOR UD-201) on ice for 3 min, and stood on ice for 2 minutes. After the procedures were repeated 4 times, the cells were lysed completely. The suspension was centrifuged at 4° C. at 13000 rpm for 20 minutes, and the supernatant was collected. The collected supernatant was centrifuged at 4° C. at 13000 rpm for 20 minutes, and the supernatant was collected as the soluble fraction.

(5) Purification with Ni Affinity Chromatography 3 mL of Ni Sepharose 6 Fast Flow (GE Healthcare) was packed in a 13.5 mL open column (GE Healthcare); after the open column was thoroughly washed with Milli-Q water, it was equilibrated by circulating a 10 mM phosphate buffer solution containing 50 mM NaCl and 20 mM imidazole (pH7.4). Each soluble fraction of Endo.Al.Ly and Exo.Al.Ly obtained by ultrasonic disruption was subjected to the equilibrated Ni Sepharose 6 Fast Flow, stirred at 4° C. overnight, to adsorb the protein to the carrier. The protein solution containing the carrier was transferred to an open column, and was flowed at a flow rate of 2 mL/min. The solution was recovered as a flow-through fraction. The column was washed with 20 mL of the same buffer as the buffer solution for equilibration, and the solution was collected as a wash fraction. Then, 20 mL of 10 mM phosphate buffer containing 50 mM NaCl and 500 mM imidazole (pH7.4) was flowed, 1 mL of each solution was collected as elution fractions. Then, 20 mL of 10 mM phosphate buffer containing 50 mM NaCl and 50 mM EDTA (pH7.4) was flowed, and was collected as a wash fraction after elution. Finally, the column was washed with 20% ethanol and stored.

The eluted fractions were subjected to SDS-PAGE, and confirmed Endo.Al.Ly and Exo.Al.Ly, respectively. The fractions containing Endo.Al.Ly and Exo.Al.Ly were each collected, and dialyzed at 4° C. overnight against 20 mM Tris-HCl buffer (pH7.5).

(6) Purification by Anion Exchange Chromatography

The protein solutions containing Endo.Al.Ly and Exo.Al.Ly after dialysis were respectively subjected to anion exchange chromatography using AKTAprime plus (GE Healthcare). For the anion exchange column, a 1 mL HiTrap Q HP (GE Healthcare) was used. Anion exchange chromatography was performed at a flow rate of 1 mL/min for all steps. After equilibrating the column with 10 mL of 20 mM Tris-HCl buffer (pH7.5), protein solutions containing dialyzed Endo.Al.Ly and Exo.Al.Ly, respectively, were flowed into the column, to absorb the target protein to the carrier. Then, the column was washed with 5 mL of 20 mM Tris-HCl buffer (pH 7.5). Then, the absorbed protein was eluted with 20 mM Tris-HCl buffer (pH7.5) containing 0 to 1.0M NaCl as a linear concentration gradient, and 1 mL elution fractions were collected. Then, the column was washed with 5 mL of 20 mM Tris-HCl buffer (pH7.5) containing 1.0 M NaCl. The eluted fractions were subjected to SDS-PAGE, and the fractions containing the target protein were collected. The protein solutions were concentrated to 10 mL using an Amicon Ultra-15 30 k MWCO (MILLIPORE) for supplying to gel filtration chromatography.

(7) Purification by Gel Filtration Chromatography

After the anion exchange chromatography, the protein solutions containing Endo.Al.Ly and Exo.Al.Ly were respectively subjected to gel filtration chromatography with AKTAprime plus (GE Healthcare). HiLoad™16/60 Superdex™75 pg (GE Healthcare) was used for the column. 120 mL of 20 mM Tris-HCl buffer containing 100 mM NaCl (pH7.5) was used at a flow rate of 0.3 mL/min for equilibration of the column. The protein solutions containing Endo.Al.Ly and Exo.Al.Ly of above (6) were respectively subjected to the column. 200 mL of 20 mM Tris-HCl buffer containing 100 mM NaCl (pH7.5) was flowed at a rate of 1 mL/min. Every 3 mL of solution was eluted. The elution fractions containing protein detected by absorbance of 280 nm were collected. The fractions containing target protein as a single band at SDS-PAGE were each collected, and dialyzed 4° C. overnight against 20 mM Tris-HCl buffer (pH7.5).

(8) Concentration Measurements

The absorbance at a wavelength of 280 nm of Endo.Al.Ly and Exo.Al.Ly was measured. Protein concentrations of Endo.Al.Ly and Exo.Al.Ly were calculated using the following equation (1) from the molar extinction coefficient E by the absorbance.

$$\varepsilon = (\#Trp) \times 5500 + (\#Tyr) \times 1490 \qquad \text{Equation (1):}$$

2. Results (1) Construction of Constructs

Figure 2:
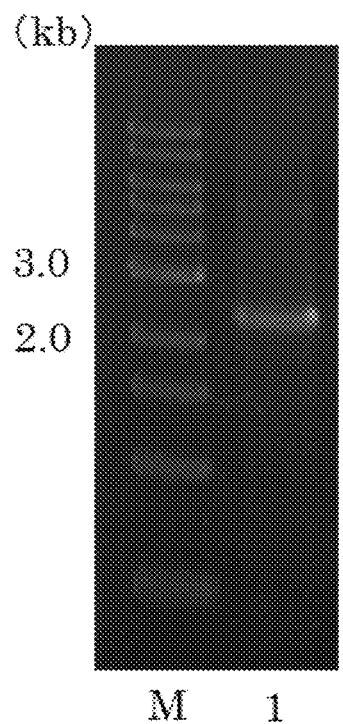
FIG. 2 is a photograph of an agarose gel electrophoresis of the Exo.Al.Ly gene amplified by PCR. Lane M is a 1 kb DNA Ladder (NEW ENGLAND Bio Labs), and Lane 1 is Exo.Al.Ly.
Figure 3:
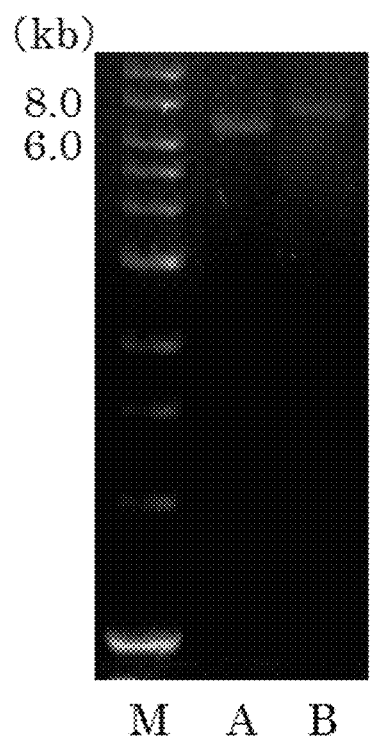
FIG. 3 is a photograph of an agarose gel electrophoresis of respective plasmids in which target genes were introduced. Lane M is a 1 kb DNA Ladder (NEW ENGLAND Bio Labs), Lane A is pET25b(+)-Endo.Al.Ly, and Lane B is pET22b(+)-Exo.Al.Ly.

FIG. 2 showed the results of agarose gel electrophoresis of Exo.Al.Ly gene amplified by PCR. After reacting with restriction enzymes, reacting with ligation enzyme, the colony that had the target gene was selected by colony PCR. After extracting the plasmid, pET22b(+)-Exo.Al.Ly (7.9 kb), in which the Exo.Al.Ly gene (2.4 kb) was introduced into the pET22b(+) vector (5.5 kb), was confirmed by agarose gel electrophoresis. Then, the plasmid pET22b(+)-Endo.Al.Ly (7.0 kb), in which the Endo.Al.Ly gene (1.5 kb) was introduced into the pET25b(+) (5.5 kb) vector, was confirmed by agarose gel electrophoresis. FIG. 3 showed the results. The constructs showed bands in the size of the expression vectors.

(2) Expression Confirmation of Endo.Al.Ly and Exo.Al.Ly

Figure 4:
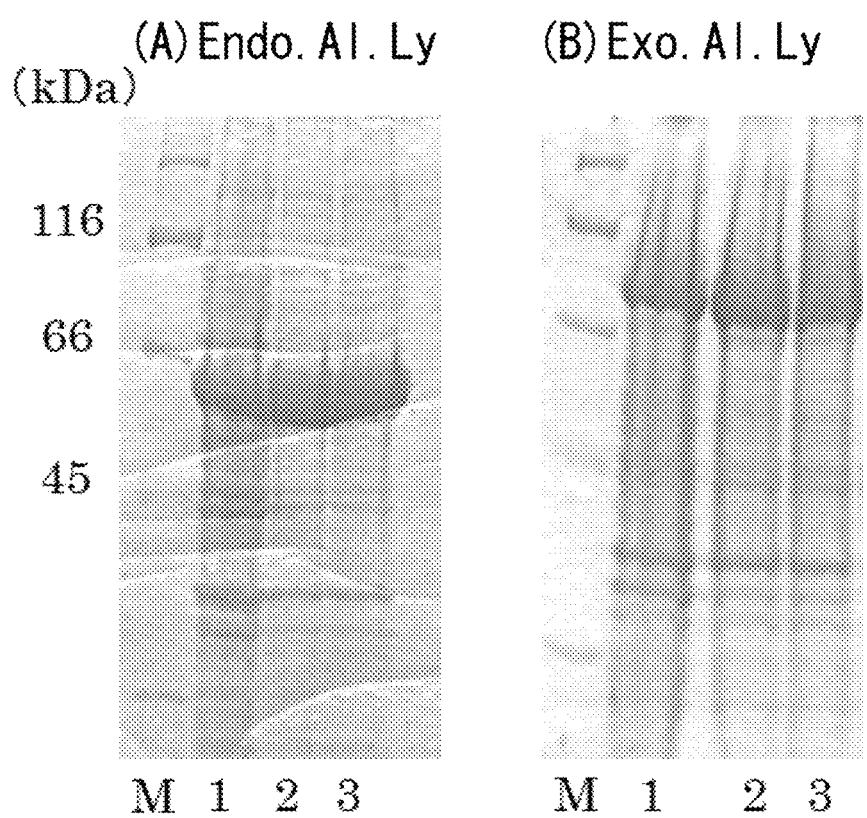
FIG. 4 is photographs of a SDS-PAGE showing the results of the confirmation of expression of (A) Endo.Al.Ly and (B) Exo.Al.Ly. Lane M is a protein marker, Lane 1 is no IPTG induction, Lane 2 is added 0.1 mM of IPTG, and Lane 3 is added 1 mM of IPTG.

The target proteins were expressed by IPTG induction. FIG. 4 showed the SDS-PAGE results of expressed proteins. Since the molecular weight of Endo.Al.Ly and Exo.Al.Ly are 89 kDa and 52 kDa, respectively, thick bands corresponding to each molecular weight in the figure were confirmed to be the target protein. Since the band pattern did not change with the concentration of IPTG, these enzymes were expressed without induction by IPTG.

(3) Large Scale Culture and Solubilization of the Enzyme Proteins

Figure 5:
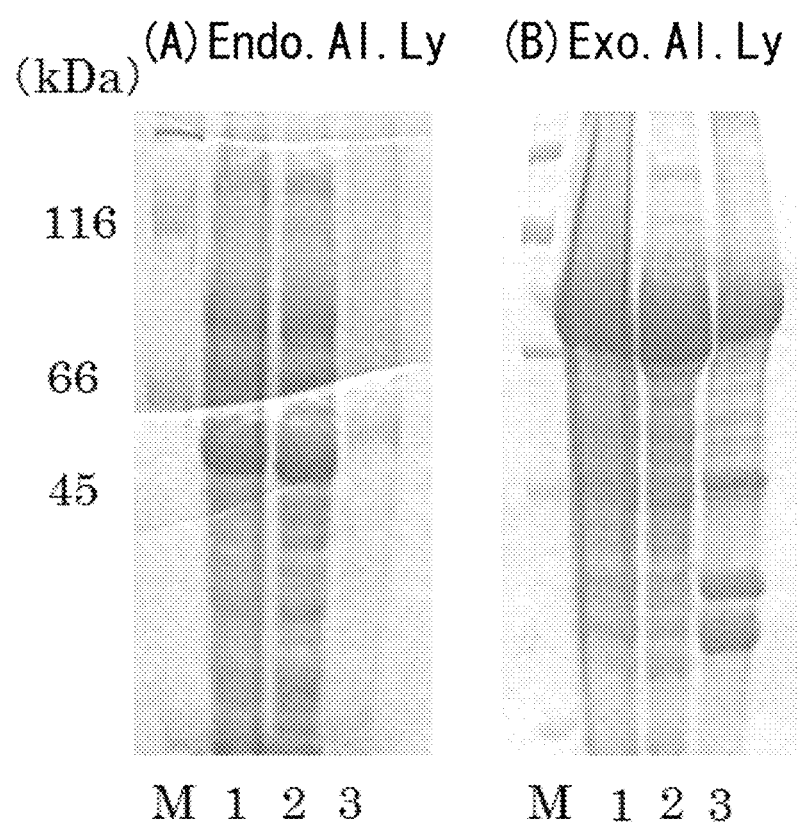
FIG. 5 is photographs of a SDS-PAGE showing the results of the confirmation of solubilization of (A) Endo.Al.Ly and (B) Exo.Al.Ly. Lane M is a protein marker, Lane 1 is the suspension before separation, Lane 2 is the soluble fraction, and Lane 3 is the insoluble fraction.

*E. coli* was cultivated in a large scale, and the obtained cells were lysed by sonication. Insoluble fractions and soluble fractions were collected separately by centrifugation. FIG. 5 showed the SDS-PAGE results for each fraction. The molecular weight of Endo.Al.Ly and Exo.Al.Ly are 89 kDa and 52 kDa respectively; thick bands corresponding to each molecular weight in the figure were the target protein. Since the target proteins were confirmed in the soluble fraction about Endo.Al.Ly and Exo.Al.Ly, sufficient solubilization was confirmed.

(4) Purification of Endo.Al.Ly and Exo.Al.Ly

Figure 6:
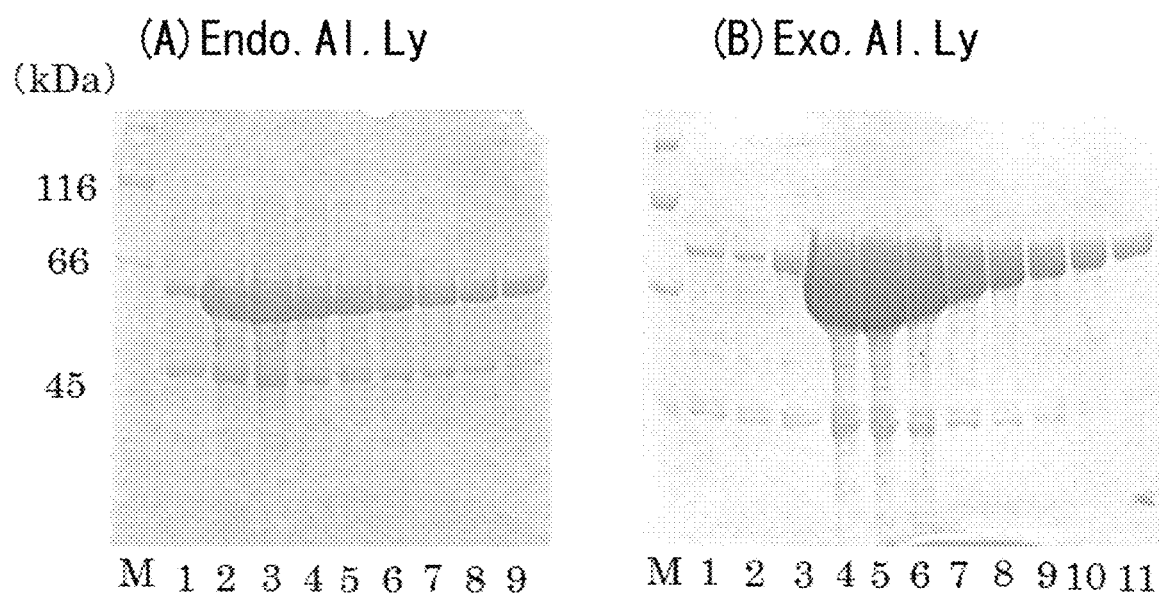
FIG. 6 shows photographs of a SDS-PAGE of (A) Endo.Al.Ly and (B) Exo.Al.Ly after purification by Ni-affinity chromatography. Lane M is a protein marker, and Lanes 1 to 11 are elution fractions.
Figure 7:
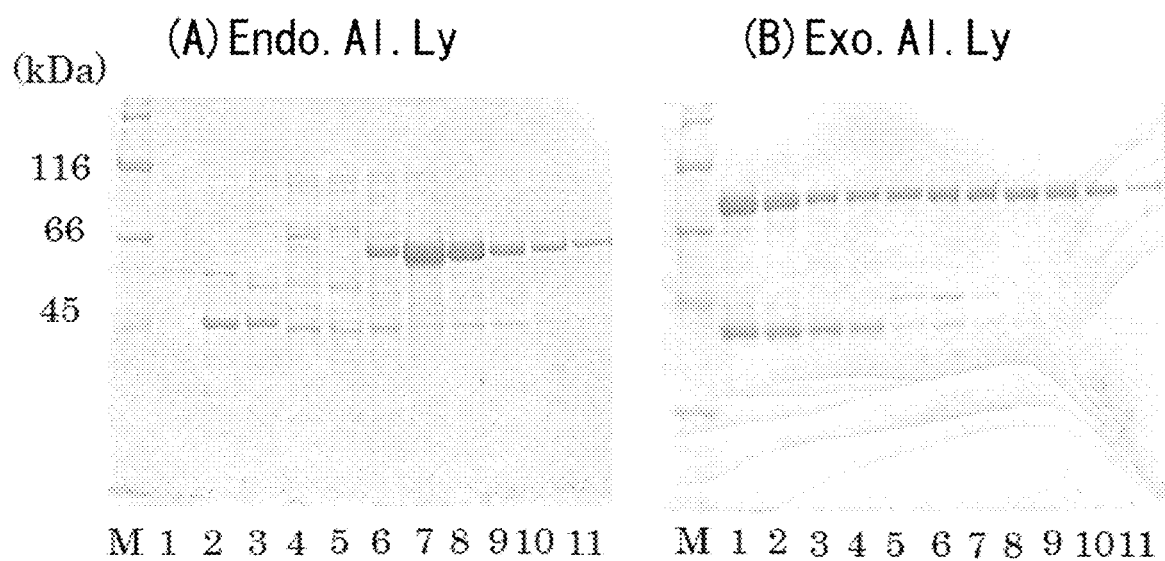
FIG. 7 shows photographs of a SDS-PAGE of (A) Endo.Al.Ly and (B) Exo.Al.Ly after purification by anion exchange chromatography. Lane M is a protein marker, and Lanes 1 to 11 are elution fractions.
Figure 8:
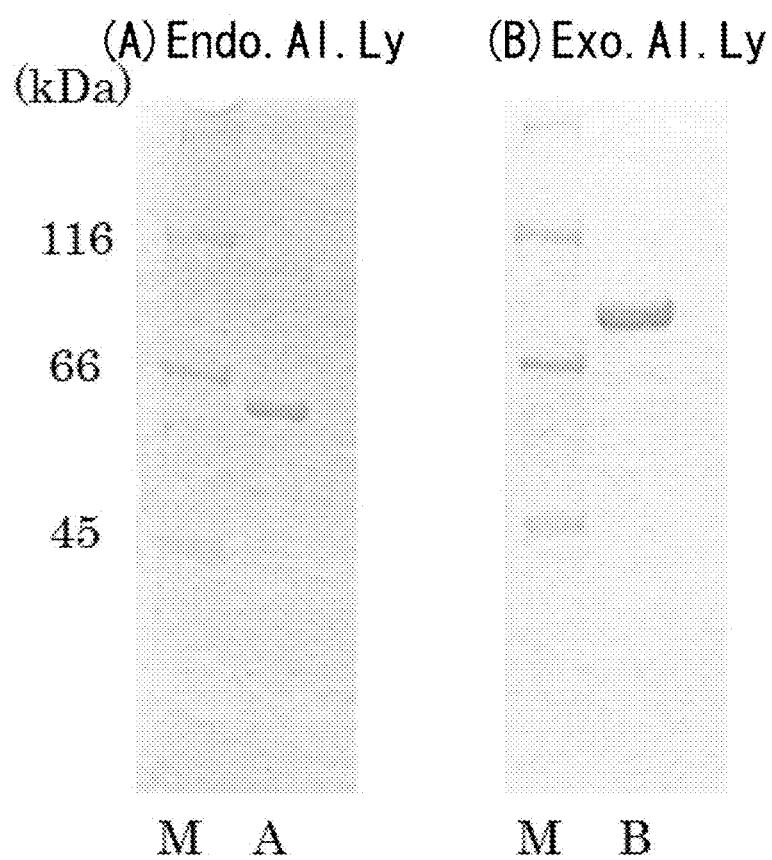
FIG. 8 shows photographs of a SDS-PAGE of (A) Endo.Al.Ly and (B) Exo.Al.Ly after purification by gel filtration chromatography. Lane M is a protein marker, Lane A is Endo.Al.Ly, and Lane B is the Exo.Al.Ly.

Since Endo.Al.Ly and Exo.Al.Ly were each expressed in the state that His-Tag was added, purification was carried out using Ni-affinity chromatography. FIG. 6 shows the SDS-PAGE electrophoresis results after purification. Since impurities could not be sufficiently removed in both proteins, further purification was carried out by anion exchange chromatography. FIG. 7 shows the SDS-PAGE electrophoresis results after purification. A relatively dark band remained at about the 45 kDa-protein-marker in both proteins. Therefore, gel filtration chromatography was carried out. FIG. 8 shows the results. By these procedures, a single band was obtained for both proteins.

After the absorbance at a wavelength of 280 nm of purified Endo.Al.Ly and Exo.Al.Ly were measured, protein concentrations were calculated. The concentrations of Endo.Al.Ly and Exo.Al.Ly were 4.0 µM and 3.7 µM, respectively. 4.7 mg of purified Endo.Al.Ly and 10.0 mg of purified Exo.Al.Ly were respectively recovered from 1 L of medium.

Thus, according to the method of this embodiment, Exo.Al.Ly and Endo.Al.Ly could be expressed and purified using *E. coli* in large scale.

Next, the enzymatic activity was determined for each enzyme protein.

<Evaluation of the Enzymatic Activity of Exo.Al.Ly and Endo.Ally and Identification of Products>

Alginate lyase belongs to polysaccharide lyases (PLs); Endo.Al.Ly and Exo.Al.Ly are classified in the PL7 family and the PL15 family, respectively. There are two types of cutting modes in alginate lyase, endo-type and exo-type. The endo-type alginate lyase cuts the glycosidic bond of alginate by beta-elimination (elimination reaction), to produce an unsaturated oligosaccharide. On the other hand, the exo-type alginate lyase recognizes the non-reducing end of unsaturated oligosaccharides of alginate or produced by endo-type alginate lyase, and cuts the bond in the order by beta-elimination. The endo-type alginate lyase belongs to the PL7 family, and the exo-type alginate lyase belongs to the PL15 family. Therefore, Endo.Al.Ly exhibits the endo-type cutting mode, and Exo.Al.Ly exhibits the exo-type cutting mode.

Therefore, after the enzymatic reaction by Endo.Al.Ly and Exo.Al.Ly was performed using sodium alginate as the substrate, the products were subjected to thin-layer chromatography to evaluate the cutting mode and degradation rate.

In addition, the products obtained by the enzymatic reaction were analyzed and evaluated by LC/MS.

1. Test Method
(1) Confirmation of Enzymatic Activities

The Endo.Al.Ly enzyme solution and Exo.Al.Ly enzyme solution prepared in the manner described above were each diluted to 0.25 mg/mL. Sodium alginate (Sigma-Aldrich), which is a soluble salt of alginate, was used as the substrate for the enzymatic reaction, and was dissolved in 1.0% (w/v) with milli Q. 1.0 mL of the diluted enzyme solution was added to 4.0 mL of the substrate solution, and an enzymatic reaction solution containing 0.8% (w/v) substrate and 0.05 mg/mL enzyme was prepared. The enzymatic reaction was performed at 25° C., and the absorbance was measured at 235 nm over time.

(2) Enzymatic Reactions

Three kinds of reaction solutions, in which 1 mL of 1.60 mg/mL Endo.Al.Ly, 1 mL of 3.82 mg/mL Exo.Al.Ly, or 1 mL of 1.60 mg/mL Endo.Al.Ly and 1 mL of 3.82 mg/mL Exo.Al.Ly were added to 10 mL of the substrate solution containing 1.0% (w/v) sodium alginate, were prepared and reacted for 3 days at 37° C. Then, the reaction solutions were ultrafiltered by Amicon Ultra-15 3000 MWCO (MILLIPORE, cut-off molecular weight 3000) to remove unreacted sodium alginate and enzyme. The enzymatic reaction solution that passed through the filter was frozen and lyophilized to obtain a powdered enzymatic reaction product. After measuring the weight of the enzymatic reaction product, the yield of enzymatic reaction product was calculated after subtracting the weight of the buffer solution (20 mM Tris-HCl) added to the enzymatic reaction.

(3) Detection of the Products by Thin Layer Chromatography (TLC)

The powdered products of Endo.Al.Ly product, Exo.Al.Ly product and Endo.Al.Ly and Exo.Al.Ly product obtained by the lyophilization in the above (2) were each dissolved in milli-Q water to be 30 mg/mL, and used as TLC samples.

As there were no commercially available standards for the monosaccharide or oligosaccharide of alginate, equal amounts of glucose as a monosaccharide and maltose as a disaccharide were mixed and dissolved in milli-Q water to be 3.0 mg/ml, which was used as a position index (marker).

5 µL of the marker and samples were each spotted on a TLC plate silica gel $60F_{254}$ (Merck). After adding a solvent containing Butanol:acetic acid:Milli Q water=2:1:1 (v/v) to the TLC chamber, the TLC plate spotted with the marker and samples was developed for about 6 hours. After development, the TLC plate was sufficiently dried and was developed again. After the TLC plate was dried, DPA reagent was sprayed. DPA reagent was prepared as follows. 4.0 g of diphenylamine was dissolved in acetone, up to a total volume of 100 mL with acetone, which was named A solution. Next, 4.0 mL of aniline was added and mixed in 96 mL of acetone, which was named B solution. 85% of phosphoric acid was named C solution. A solution:B solution:C solution=5:5:1 ratio were added and prepared as the DPA reagent. After spraying the DPA reagent, the TLC plate was dried and heated on a hot plate for 10 minutes to detect the products by the enzymes.

(4) Identification of the Products of LC/MS Analysis

Powdered Exo.Al.Ly product, and Endo.Al.Ly and Exo.Al.Ly product obtained by lyophilizing after the enzymatic reaction in the above (2), were analyzed by LC/MS. The total ion chromatogram (TIC), which was an integrated total signal of all mass numbers, and the selective ion monitoring (SIM) specified mass number of deprotonated monosaccharide (DEH) produced by decomposition of the alginate lyase by negative mode (m/z=175), were measured.

Detailed analysis conditions of LC/MS were as follows.
(i) LC/MS Conditions
Column: Shodex IC NI-424 (internal diameter 4.6 mm×length 100 mm)
Mobile phase: 40 mM ammonium formate buffer containing 0.1% formic acid
Flow rate: 0.5 mL/min
Column oven: 40° C.
LC-MS: Agilent 1260HPLC+Agilent 6120 single quadrupole mass spectrometer
Ionization method: ESI/APCI multimode, negative measurement
MS conditions: dry gas: 12.0 L/min, nebulizer: 35 psi, dry temperature: 250° C., vapolizer: 200° C., scan range: m/z 100 to m/z 1000
(ii) Identification of DEH In negative measurement of LC-MS SIM mode (selective ion monitoring mode), m/z 175 (corresponds to deprotonated ion of DEH [M-H]) was selected. Since the retention times of the detected peaks by TIC (detection of all compounds contained in the sample) and by the SIM mode completely matched, the degradation product of Exo.Al.Ly and the degradation product of Exo.Al.Ly and Endo.Al.Ly were identified as DEH.

(5) Confirmation of Substrate Specificity

Three kinds of reaction solutions, in which 1 mL of 0.20 mg/mL Endo.Al.Ly, 1 mL of 0.20 mg/mL Exo.Al.Ly, or 1 mL of Endo.Al.Ly and 1 mL of Exo.Al.Ly were added to 10 mL of the substrate solution containing 1.0% (w/v) poly beta-D-mannuronic acid (polyM) or poly alpha-L-guluronic acid (polyG), were prepared and reacted for 3 days at 37° C.

Then, the same treatments were carried out according to the above "(2) Enzymatic reactions" and "(3) Detection of the products by thin layer chromatography (TLC)".

2. Results (1) Confirmation of Enzymatic Activity

Figure 9:
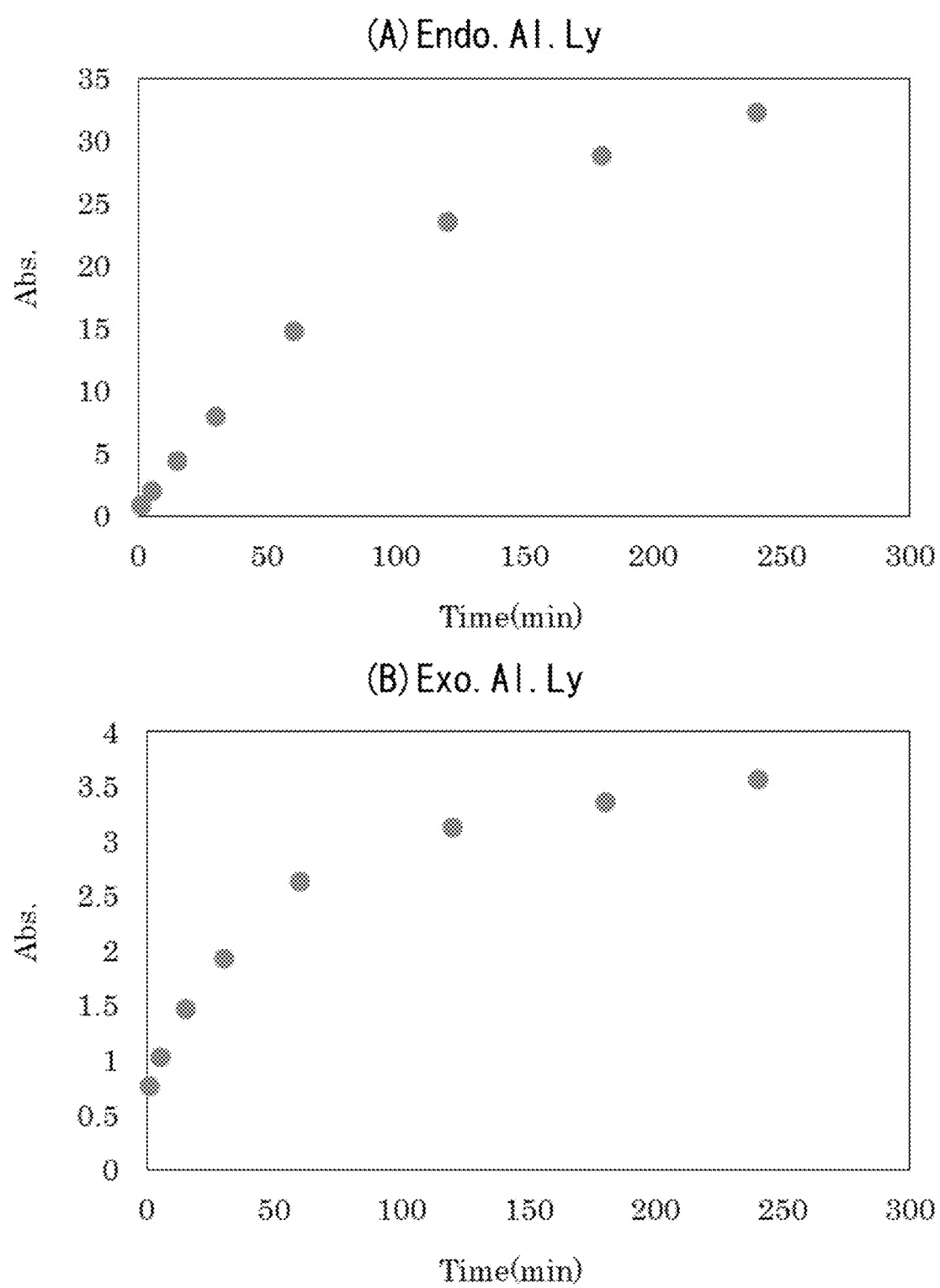
FIG. 9 is graphs showing the results of the confirmation of the enzymatic activities of (A) Endo.Al.Ly and (B) Exo.Al.Ly.

FIG. 9 shows a graph of the change in absorbance at 235 nm over time. Furthermore, the absorbance at 24 hours and 48 hours after the start of the reaction were 40.7 after 24 hours and 51.2 after 48 hours by Endo.Al.Ly, and 1.37 after 24 hours and 1.58 after 48 hours by Exo.Al.Ly. As shown in FIG. 9, since the absorbance at 235 nm of the reaction solutions after the initiation of both Endo.Al.Ly and Exo.Al.Ly increased over time, the two enzymes were confirmed to exhibit the activity of decomposing sodium alginate into unsaturated sugar. Also, the absorbance after 24 and 48 hours showed an increase by Endo.Al.Ly, and a decrease by Exo.Al.Ly. This was because Endo.Al.Ly of the endo-type enzyme continued to produce unsaturated sugars by the elimination reaction, whereas Exo.Al.Ly of the exo-type enzyme cut the unsaturated uronic acid residues from the ends in order, to open unsaturated monosaccharide rings, to make DEH, and to cleave unsaturated double bonds.

(2) Enzymatic Reaction

Three kinds of reaction solutions, in which Endo.Al.Ly only, Exo.Al.Ly only, or Endo.Al.Ly and Exo.Al.Ly were contained, were prepared and reacted for 3 days, ultrafiltered, frozen and lyophilized to obtain powdered products. After subtracting the weight of the buffer solution (20 mM Tris-HCl), the yield of products was 16.4 mg by Endo.Al.Ly only, 64.0 mg by Exo.Al.Ly only, and 83.8 mg by Endo-.Al.Ly and Exo.Al.Ly. Since the substrate used in the enzymatic reaction was 100 mg, the yield was 16.4%, 64.0%, and 83.8%, respectively. It is noted that, when the addition amount of Exo.Al.Ly was doupled or tripled and the addition amount of Endo.Al.LY was made the same, the yield was almost the same as above (about 85%).

When endo-type alginate lyase Alg7D (PL7) from *Saccharophagus degradans* and exo-type alginate lyase Alg17C (PL17) were reacted with sodium alginate as a substrate, it was reported that DEH was obtained 45.5% yield (non Patent Document 6). However, the enzymatic reaction by the combination of Endo.Al.Ly and Exo.Al.Ly could be obtained DEH in 83.8% yield which was a 1.8 times higher value.

(3) Detection of the Products by Thin-Layer Chromatography (TLC)

Figure 10:
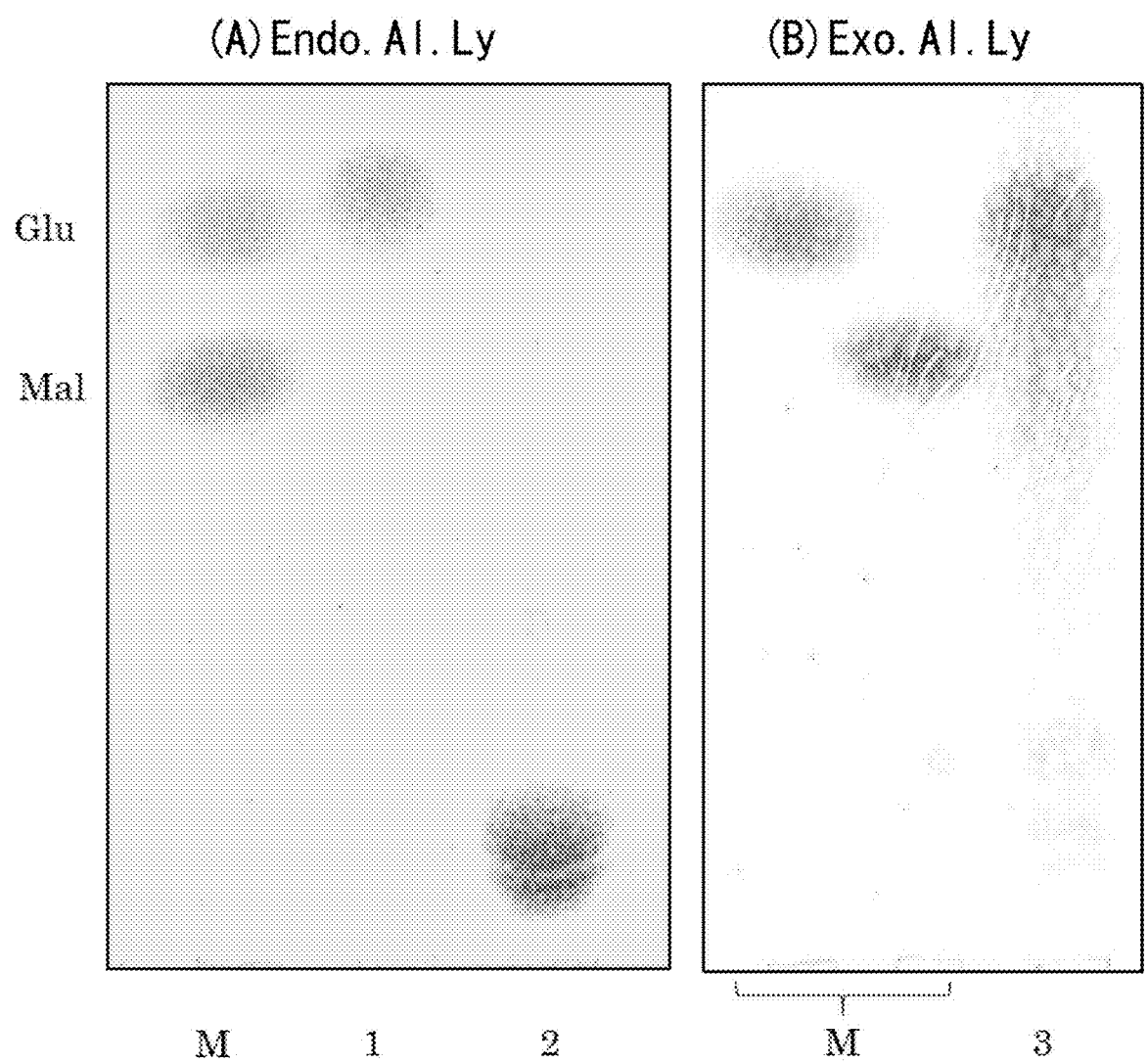
FIG. 10 is photographs showing the results of a TLC of (A) Endo.Al.Ly, (B) Exo.Al.Ly and a combination of (A) and (B). Lane M is a marker (Glucose (Glu), Maltose (Maltose)), Lane 1 is the product by Exo.Al.Ly, Lane 2 is the product by Endo.Al.Ly, and Lane 3 is the product by Endo.Al.Ly and Exo.Al.Ly.

The products obtained by enzymatic reaction by Endo-.Al.Ly only, Exo.Al.Ly only, and the Endo.Al.Ly and Exo.Al.Ly mixture were spotted on a TLC plate and detected by TLC. The yield of the enzymatic reactions was confirmed. FIG. 10 shows the results of TLC. The products by Endo.Al.Ly showed two overlapping spots, and they were at a lower position than that of maltose serving as an indicator of a disaccharide. The data and the results in the above (1) (i.e., increase of absorbance at 235 nm) showed that the products of Endo.Al.Ly were alginate unsaturated oligosaccharides. The product by Exo.Al.Ly showed a single spot at a position equivalent to that of glucose severing as an indicator of a monosaccharide. Also, the product by both Endo.Al.Ly and Exo.Al.Ly showed a dark spot at the same position as glucose. The product showed tailing of the spot. The cause of tailing was considered to be the concentration of DEH; because it was higher than expected, it was not completely developed by the solvent.

(4) Identification of the Products by LC/MS Analysis

Figure 11:
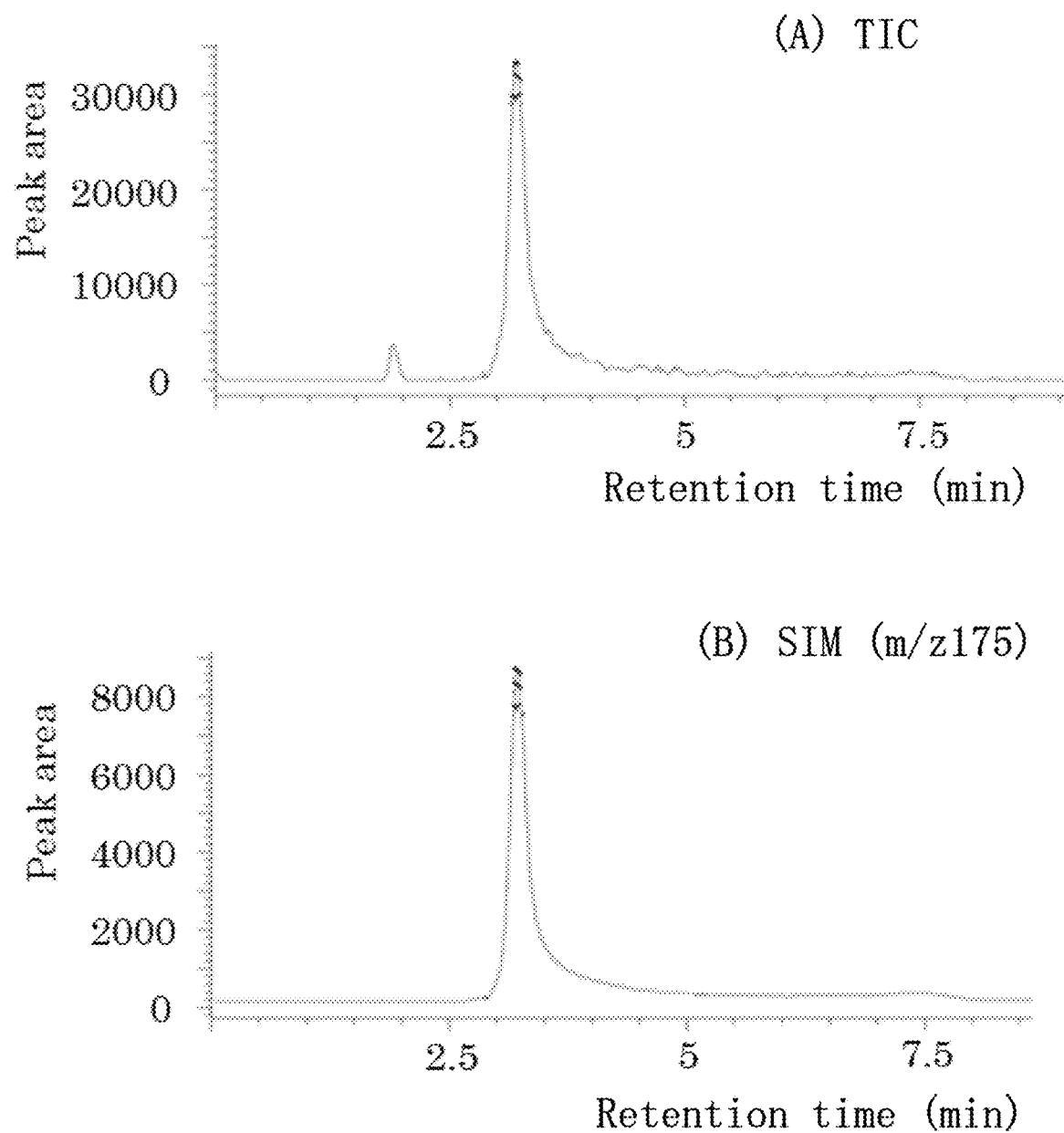
FIG. 11 is chromatograms showing the results of the measurements of the product by Exo.Al.Ly by LC/MS. (A) is the result of TIC, and (B) is the result of SIM mode (m/z 175).

FIG. 11 shows the results of the analysis of the products by Exo.Al.Ly using LC/MS of measurement by the TIC and SIM modes. In the results of TIC, the small peak observed around at 1.8 min was that derived from the mobile phase. Therefore, the peak of the product was confirmed to be a peak near 3.2 min. Further, in the results of the SIM mode in which the mass number of deprotonated DEH was specified, only one peak at about 3.2 min was confirmed. Since the mass number was specified in the SIM mode, the peak was due to DEH. Moreover, since the retention time of the peak completely matched with that of TIC, and the peak of TIC showed only one, the product by Exo.Al.Ly was confirmed to be only DEH. Further, Shodex IC I-524A instead of Shodex IC NI-424 was used as the column for the anion analysis, and similar results were obtained without the use of gradient conditions in LC. Therefore, similar results would be obtained with the use of commercially available anion analytical columns.

Figure 12:
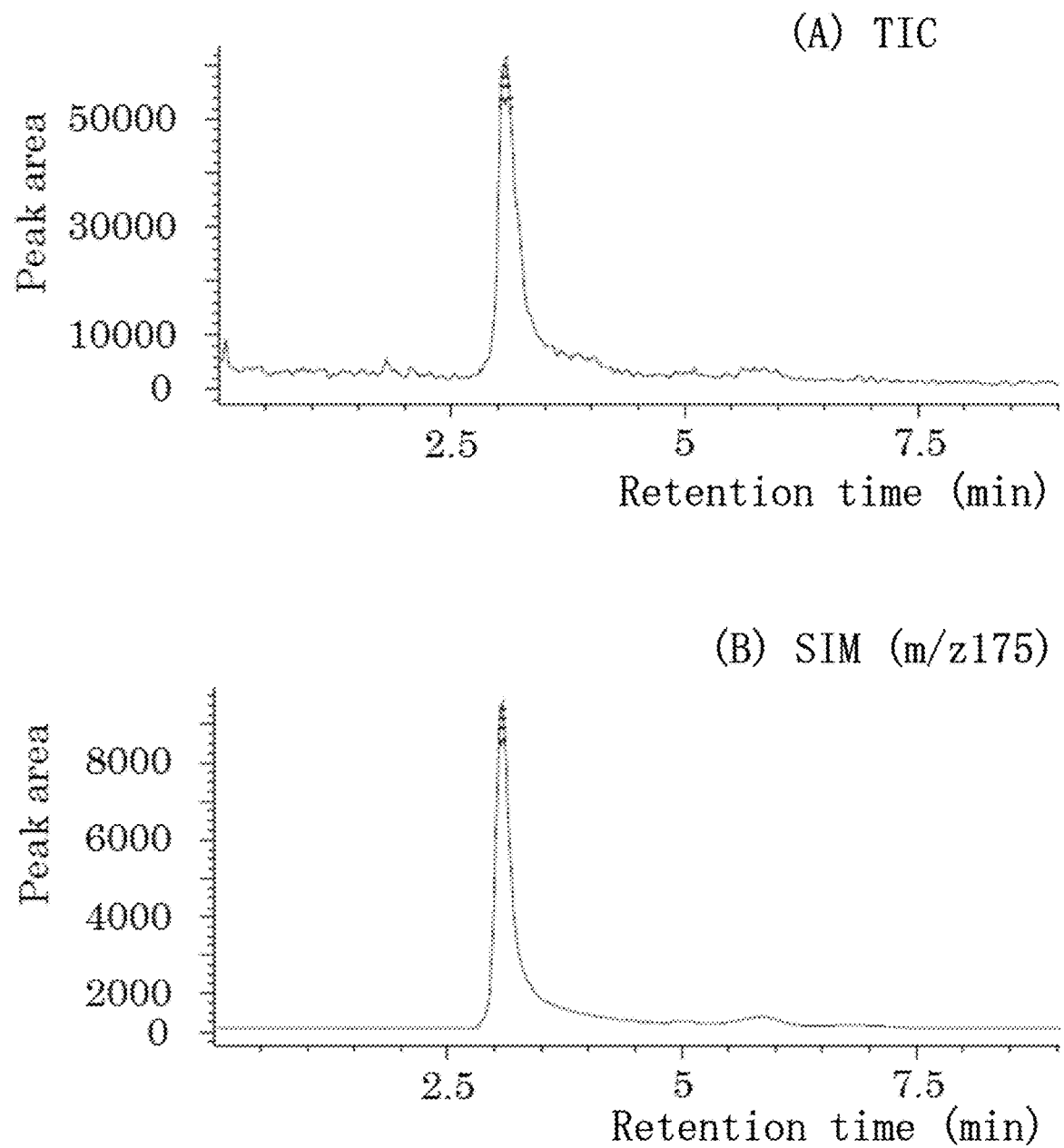
FIG. 12 is chromatograms showing the results of the measurements of the product by Endo.Al.Ly and Exo.Al.Ly by LC/MS. (A) is the result of TIC, and (B) is the result of SIM mode (m/z 175).
Figure 13:
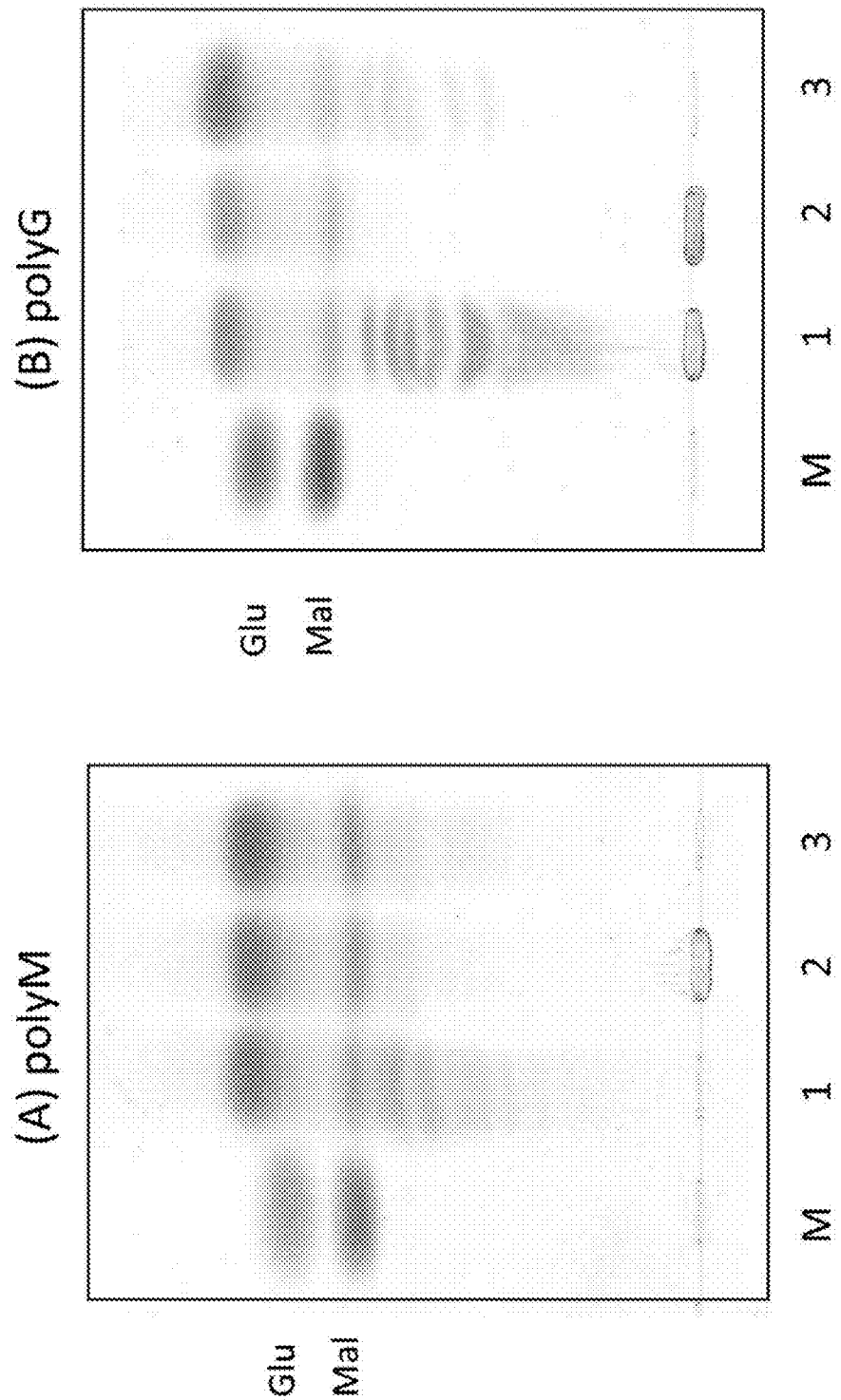
FIG. 13 is photographs showing the results of a TLC confirming the degradation activities by Exo.Al.Ly or Exo.Al.Ly and Endo.Al.Ly using (A) PolyM or (B) PolyG as the substrate. Lane M is a marker (glucose (Glu), maltose (Mal)), Lane 1 is the product by Endo.Al.Ly, Lane 2 is the product by Exo.Al.Ly, and Lane 3 is the product by Endo.Al.Ly and Exo.Al.Ly.

Then, FIG. 12 shows the results of measuring the product by Endo.Al.Ly and Exo.Al.Ly using the TIC and SIM modes with LC/MS. The measurement results showed substantially the same as those with regard to the product by Exo.Al.Ly using the TIC and SIM mode (FIG. 11). Therefore, it was determined that the product with both Endo.Al.Ly and Exo.Al.Ly was also only DEH.

(5) Confirmation of Substrate Specificity

When Endo.Al.Ly, Exo.Al.Ly and both enzymes were reacted with polyM or polyG as the substrate, similar degradation activity for both substrate was shown. Conventional alginate lyase may exhibit a specific reaction against polyM or polyG. However, for the alginate lyase of the embodiments, the specificity for both substrates was not observed, and was found to react substantially equally.

Thus, according to the embodiments, novel exo-type alginate lyase (Exo.Al.Ly) and endo-type alginate lyase (Endo.Al.Ly) could be produced in a large scale, and a method for producing unsaturated uronic acid monosaccharide (DEH) using the enzymes was provided.

The invention claimed is:

1. A DNA sequence encoding a polypeptide having the amino acid sequence shown in SEQ ID NO:1 and either a His-Tag or the amino acid sequence shown in SEQ ID NO:7 attached to the C-terminus of the amino acid sequence of SEQ ID NO:1, the polypeptide exhibiting exo-type alginate lyase activity.

2. An expression vector including a DNA sequence encoding a polypeptide having the amino acid sequence shown in SEQ ID NO:1 and either a His-Tag or the amino acid sequence shown in SEQ ID NO:7 attached to the C-terminus of the amino acid sequence of SEQ ID NO:1, the expression vector being in a state capable of expressing the polypeptide.

3. The expression vector according to claim 2, wherein the DNA sequence comprises the DNA sequence as shown in SEQ ID NO: 8.

4. A transformed host cell genetically modified to express the expression vector of claim 3.

5. The transformed host cell according to claim 4, wherein the transformed host cell is *E. coli*.

6. A transformed host cell genetically modified to express the expression vector of claim 2.

7. The transformed host cell according to claim 6, wherein the transformed host cell is *E. coli*.

8. The DNA sequence according to claim 1, wherein the DNA sequence comprises the DNA sequence as shown in SEQ ID NO: 8.

9. The DNA sequence according to claim 1, wherein the amino acid sequence shown in SEQ ID NO: 7 is attached to C'-terminus of the amino acid sequence of SEQ ID NO:1.

10. The expression vector according to claim 2, wherein the amino acid sequence shown in SEQ ID NO: 7 is attached to C'-terminus of the amino acid sequence of SEQ ID NO:1.

* * * * *

SEQUENCE LISTING

<160> NUMBER OF SEQ ID NOS: 8

<210> SEQ ID NO 1
<211> LENGTH: 785
<212> TYPE: PRT
<213> ORGANISM: Falsirhodobacter sp. alg1

<400> SEQUENCE: 1

```
Met Ser Thr Glu Asn Lys Ser Arg Ser Asn Leu Phe Pro Leu Asp Glu
1               5                   10                  15

Pro Lys Ala Gly Arg Leu Thr Ile Gln Tyr Gly Pro Leu Glu Thr Thr
                20                  25                  30

Thr Leu Ile Glu Asn Pro Pro Arg Phe Ser Trp Leu Pro Val Ile Glu
            35                  40                  45

Asp Gly Ala Thr Tyr Ala Leu Arg Ile Ser Thr Asp Pro Glu Tyr Ser
        50                  55                  60

Ala Ala Asn Thr Leu Leu Phe Ser Gly Ile Gln Leu Asn Phe Phe Thr
65                  70                  75                  80

Pro Asp Ala Pro Leu Ala Ala Gly Thr Trp Tyr Trp Ser Tyr Ala Gln
                85                  90                  95

Cys Asp Ala Ser Gly Lys Pro Val Thr Glu Trp Ser Thr Ser Arg Arg
                100                 105                 110

Ile Thr Leu Asp Glu Gly Leu Pro Gln Thr Pro Leu Ala Pro Arg Lys
            115                 120                 125

Thr Arg Phe Asp Ala Ala Thr Arg Ala His Pro Arg Leu Trp Met Asp
        130                 135                 140

Gly Gly Arg Leu Glu Gln Phe Arg Lys Asp Val Ala Ala Asp Pro Thr
145                 150                 155                 160

His Cys Thr Trp Ser Thr Phe Phe Glu Gly Ser Val Leu Pro Trp Met
                165                 170                 175

Asp Arg Asp Ile Ile Glu Glu Pro Val Gly Tyr Pro Asp His Lys Arg
            180                 185                 190

Val Ala Lys Ile Trp Arg Lys Val Tyr Ile Glu Cys Gln Glu Leu Met
        195                 200                 205

Tyr Ala Ile Arg His Leu Ala Val Gly Gly Val Thr Gln Asp Ala
210                 215                 220

Ala Met Leu Ala Arg Ala Lys Glu Trp Leu Leu Ser Ala Ala Arg Trp
225                 230                 235                 240

Asn Pro Ala Gly Thr Thr Ser Arg Ala Tyr Thr Asp Glu Trp Ala Phe
                245                 250                 255

Arg Val Asn Leu Ala Leu Ala Trp Gly Tyr Asp Trp Leu Tyr Asp Gln
            260                 265                 270

Leu Asp Glu Asp Glu Arg Thr Leu Val Arg Thr Ala Leu Leu Glu Arg
        275                 280                 285

Thr Arg Gln Thr Ala Asp His Leu Met Arg His Ala Ser Ile His Leu
290                 295                 300

Phe Pro Phe Asp Ser His Ala Val Arg Ala Val Ser Ala Val Leu Ile
305                 310                 315                 320

Pro Ala Cys Ile Ala Leu Leu Asp Asp Glu Pro Glu Ala Glu Asp Trp
                325                 330                 335

Leu Asn Tyr Ala Val Glu Phe Leu Phe Thr Val Tyr Ser Pro Trp Gly
            340                 345                 350

Asp His Asp Gly Gly Trp Ala Glu Gly Pro His Tyr Trp Met Thr Gly
        355                 360                 365

Met Ala Tyr Leu Ile Asp Ala Ala Asn Leu Leu Arg Gly Trp Ser Gly
370                 375                 380

Ile Asp Leu Tyr Gln Arg Pro Phe Gln Lys Thr Gly Asp Phe Pro
385                 390                 395                 400

Leu Tyr Thr Lys Ala Pro Asp Thr Arg Arg Ala Thr Phe Gly Asp Asp
                405                 410                 415
```

Ser Thr Met Gly Asp Leu Pro Ala Ile Lys Val Gly Tyr Asn Leu Arg
                420                 425                 430

Gln Tyr Ala Gly Val Thr Gly Asn Gly Ala Tyr Gln Trp Tyr Tyr Asp
            435                 440                 445

Glu Ile Leu Arg Thr Asn Pro Gly Thr Glu Met Ala Phe Tyr Asn Trp
        450                 455                 460

Gly Trp Trp Asp Phe Arg Phe Asp Glu Met Leu Tyr Arg Thr Asp Phe
465                 470                 475                 480

Pro Ile Val Glu Ala Val Pro Pro Ala Asp Glu Asp Ala Leu Arg Trp
                485                 490                 495

Phe Lys Gly Ile Gly Trp Val Ala Ile Gln His Arg Met Gln Ala Pro
            500                 505                 510

Asp Glu His Val Gln Phe Val Phe Lys Ser Ser Pro Tyr Gly Ser Ile
        515                 520                 525

Ser His Ser His Gly Asp Gln Asn Ala Phe Cys Leu Ser Ala Phe Gly
    530                 535                 540

Glu Asp Leu Ala Ile Gln Ser Gly His Tyr Val Ala Phe Asn Ser Thr
545                 550                 555                 560

Met His Gln Asn Trp Arg Arg Gln Thr Leu Ser Lys Asn Ala Ile Leu
                565                 570                 575

Ile Asp Gly Lys Gly Gln Tyr Ala Gly Lys Asp Lys Ala Ile Ala Met
            580                 585                 590

Gln Ser Thr Gly Lys Val Asn Ile Ala Glu Asp Arg Gly Asp His Ile
        595                 600                 605

Phe Leu Gln Gly Asp Ala Thr Glu Ala Tyr Arg Thr Leu Ser Pro Glu
    610                 615                 620

Val Arg Ser Val Val Arg Asp Val Tyr Phe Val Asn Arg Glu Tyr Phe
625                 630                 635                 640

Val Ile Val Asp Ala Ile Asp Ala Asp Thr Pro Val Ser Ile Asp Trp
                645                 650                 655

Arg Leu His Ala Asn Ala Pro Phe Asn Leu Gly Asp Ser Ser Phe Arg
            660                 665                 670

Tyr Thr Gly Glu Lys Ala Gly Phe Tyr Gly Gln Ile Leu Trp Ser Glu
        675                 680                 685

Ala Gly Pro Ala Glu Leu Thr Gln Glu Thr Gly Phe Pro Asp Val Asp
    690                 695                 700

Pro Ser Glu Ile Glu Gly Leu Pro Val Ser Thr Cys Leu Thr Ala Arg
705                 710                 715                 720

Phe Pro Lys Ser Thr Arg His Arg Ile Ala Thr Leu Ile Val Pro Tyr
                725                 730                 735

Ala Leu Asp Ala Pro Arg Arg Ile Phe Ser Phe Leu Asp Asp Gln Gly
            740                 745                 750

Tyr Asp Cys Asp Leu Tyr Phe Thr Asp Ala Asn Asp Asn Ser Phe Arg
        755                 760                 765

Val Ile Val Pro Lys Thr Phe Asp Val Gly Thr Pro Gly Ile Lys Asn
    770                 775                 780

Asn
785

<210> SEQ ID NO 2
<211> LENGTH: 484
<212> TYPE: PRT
<213> ORGANISM: Falsirhodobacter sp. alg1

<400> SEQUENCE: 2

-continued

```
Met Ser Leu Lys Leu Arg Thr Phe Cys Leu Ala Gly Thr Ala Thr Ile
1               5                   10                  15

Phe Val Ala Leu Pro Ser Thr Tyr Ala Leu Ala Ala Gly Thr Gly Ala
                20                  25                  30

Cys Thr Gly Val Ser Gln Leu Ala Ile Val Ser Ala Ser Asp Asp Gly
            35                  40                  45

Thr Phe Asp Asp Ile Tyr Ala Pro Glu Phe Ala Ile Asp Gly Glu Phe
        50                  55                  60

Gly Pro Ser Ser Arg Trp Ser Ser Leu Gly Glu Gly Lys Gln Leu Val
65                      70                  75                  80

Leu Asp Leu Gly Glu Pro Gln Thr Val Ser Glu Val Gly Leu Ala Trp
                    85                  90                  95

Tyr Lys Gly Asn Glu Arg Thr Ser Ser Phe Thr Leu Glu Ala Ser Asn
                100                 105                 110

Asp Gly Glu Asn Trp Met Pro Leu Met Asp Arg Thr Glu Ser Ala Gly
            115                 120                 125

Lys Ser Glu Ala Val Glu Lys Tyr Ser Phe Asp Ala Thr Glu Ala Arg
    130                 135                 140

Tyr Val Arg Val Thr Gly Met Gly Asn Ser Ala Ser Gly Trp Asn Ser
145                 150                 155                 160

Leu Tyr Glu Ala Gln Val Phe Gly Cys Gly Ser Gly Glu Ile Ala Ala
                165                 170                 175

Thr Gly Asp Gly Ser Gly Glu Val Lys Glu Ala Asp Val Ser Ala Tyr
            180                 185                 190

Gly Leu Arg Thr Asp Val Pro Pro Ser Glu Asn Phe Asp Leu Thr His
        195                 200                 205

Trp Lys Leu Thr Leu Pro Ala Asp Arg Asp Asn Asp Gly Lys Val Asp
    210                 215                 220

Glu Ile Glu Glu Glu Leu Gln Gly Trp Ser Asp Pro Arg Phe Phe
225                 230                 235                 240

Tyr Thr Asp Pro Ala Thr Gly Gly Met Val Phe Arg Thr Ala Pro Asp
                245                 250                 255

Gly Lys Thr Thr Ser Gly Ser His Tyr Thr Arg Ser Glu Leu Arg Glu
            260                 265                 270

Met Ile Arg Gly Gly Asp Lys Ser Ile Ala Thr Arg Val Asp Asp Gly
        275                 280                 285

Thr Pro Asn Lys Asn Asn Trp Val Phe Ser Thr Ala Pro Glu Glu Ala
    290                 295                 300

Gln Ala Leu Ala Gly Val Asp Gly Thr Met Thr Ala Thr Leu Ala
305                 310                 315                 320

Val Asn His Val Thr Arg Thr Gly Glu Ser Gly Lys Ile Gly Arg Val
                325                 330                 335

Ile Ile Gly Gln Ile His Ala Met Asp Asp Glu Pro Ile Arg Leu Tyr
            340                 345                 350

Tyr Arg Lys Leu Pro Thr Asn Lys Tyr Gly Ser Ile Tyr Phe Ala His
        355                 360                 365

Glu Pro Val Gly Gly Asp Asp Asp Leu Val Asn Val Ile Gly Asp Arg
    370                 375                 380

Gly Ser Asp Ile Asp Asn Pro Ala Asp Gly Ile Ala Leu Asp Glu Val
385                 390                 395                 400

Phe Ser Tyr Glu Ile Lys Val Thr Ser Glu Glu Lys Asp Gly Glu Leu
                405                 410                 415
```

His Pro Ile Leu Asn Val Ser Ile Thr Arg Asp Asp Gly Thr Val Val
            420                 425                 430

Lys Ala Glu Pro Tyr Asp Met Phe Glu Ser Gly Tyr Ser Thr Asp Lys
        435                 440                 445

Asp Phe Met Tyr Phe Lys Ala Gly Ala Tyr Ser Gln Asn Asn Ser Ile
    450                 455                 460

Thr Trp Pro Asp Asp Phe Asp Gln Val Thr Phe Tyr Ala Leu Asp Val
465                 470                 475                 480

Thr His Gly Glu

<210> SEQ ID NO 3
<211> LENGTH: 2358
<212> TYPE: DNA
<213> ORGANISM: Falsirhodobacter sp. alg1

<400> SEQUENCE: 3

| | | | | | |
|---|---|---|---|---|---|
| atgtcgacgg | aaaacaaatc | ccgttcaaac | ctgtttccac | ttgatgagcc | caaagcggga | 60 |
| cggctgacga | tccaatatgg | cccgctcgaa | acgacgacgc | tgattgaaaa | cccgccacgc | 120 |
| ttctcatggc | tgccggtcat | cgaggatggc | gcaacctatg | cgctgcgcat | ctcgaccgat | 180 |
| cccgaatatt | ccgcggcaaa | caccctcctg | ttttcgggca | tccagctgaa | cttcttcacg | 240 |
| cctgatgcac | ctttggcggc | aggcacttgg | tactggtcct | atgcacaatg | cgatgcctcg | 300 |
| ggaaagcccg | ttaccgaatg | gagcacgagc | cgtcgcatca | ctctcgacga | gggtctgcca | 360 |
| cagacaccgc | tggcaccacg | caagacgcgt | tttgacgcgg | cgacccgtgc | gcacccgcgc | 420 |
| ctgtggatgg | acgcggccg | gctggaacag | ttccgcaagg | atgttgccgc | cgacccgacg | 480 |
| cattgcacat | ggtctacctt | tttcgagggt | tcggttctgc | cgtggatgga | ccgcgacatc | 540 |
| atcgaagagc | ctgtgggcta | tccggatcac | aagcgtgtcg | cgaagatctg | cgcaaggtc | 600 |
| tacatcgagt | gtcaggaact | gatgtatgcg | atccgccacc | ttgctgtggg | cggtcaggtt | 660 |
| acccaggacg | cggcaatgct | ggcacgcgcc | aaggaatggc | tgctcagcgc | cgcacgctgg | 720 |
| aatccggcag | gcaccacctc | gcgcgcctat | accgatgaat | gggctttccg | tgtgaacctc | 780 |
| gcactcgcat | ggggttatga | ctggctctat | gaccagctgg | acgaggatga | gcgtacgctg | 840 |
| gtccgcaccg | ccttgctgga | gcgtacgcgc | cagacggcgg | atcacctgat | gcgccacgcc | 900 |
| agcatccacc | tgtttccgtt | tgacagccac | gctgtccgcg | cggtgtctgc | ggttctgatc | 960 |
| cccgcctgta | ttgccttgct | ggatgatgaa | cccgaggccg | aggactggct | gaactatgcg | 1020 |
| gtggaattcc | tgttcaccgt | ctattcgccg | tgggcgatc | atgacggtgg | ctgggccgag | 1080 |
| ggtccgcact | actggatgac | gggtatggcc | tatctgatcg | acgcggcaaa | cctgctgcgc | 1140 |
| ggctggagcg | gaatcgacct | gtaccaacgc | ccgttcttcc | agaaaaccgg | ggacttcccg | 1200 |
| ctttatacca | aggcgccgga | cacacgtcgg | gccacattcg | gcgatgatag | caccatgggc | 1260 |
| gatctgcccg | cgatcaaggt | cggatataac | ctgcgtcaat | acgcagggt | gaccggcaac | 1320 |
| ggtgcctacc | aatggtacta | cgacgaaatc | ctgcgcacca | cccccggcac | ggaaatggcc | 1380 |
| ttctacaact | ggggctggtg | ggatttccgg | tttgacgaaa | tgctctaccg | cacggacttc | 1440 |
| ccgatcgtag | aggcagttcc | gcccgcggat | gaggatgcac | tgcgctggtt | caagggcatc | 1500 |
| ggttgggtcg | cgatccagca | ccgtatgcag | gcaccggacg | agcatgttca | attcgtgttc | 1560 |
| aaatcctctc | cctacggctc | gatcagccaa | agccatgggg | atcagaacgc | gttctgtctg | 1620 |
| tcggcattcg | gtgaggatct | tgcaatccag | tccggccatt | atgtcgcctt | caactcgaca | 1680 |
| atgcaccaga | actggcgtcg | ccagacgctg | tcgaagaacg | ccatcctgat | cgacggaaaa | 1740 |

| | |
|---|---:|
| ggccagtacg ccggcaagga caaggcgatt gccatgcaat cgaccggtaa ggtcaatatt | 1800 |
| gccgaggatc gtggcgatca tatcttcctg caggggatg cgaccgaagc ctatcgcaca | 1860 |
| ttgtcacccg aggtccgctc ggttgtccgt gatgtgtatt tcgtgaatcg cgaatatttc | 1920 |
| gtgatcgtgg atgccatcga tgcggatacg cccgtcagca tcgactggcg tctgcacgcg | 1980 |
| aatgctccgt tcaatctggg tgatagcagc ttccgctata ccggtgaaaa ggccggtttc | 2040 |
| tatggccaga tcctgtggtc cgaggcgggt cctgccgaac tgacgcagga accggcttt | 2100 |
| ccggatgtcg atccgagcga aatcgaggga ctgccggtca gcacctgcct gaccgcccgt | 2160 |
| ttccccaaat ccacccgtca tcgtatcgcg accttgatcg tcccgtatgc tctggatgcg | 2220 |
| ccgcgccgca ttttcagctt ccttgatgat cagggttacg actgcgatct ctatttcacc | 2280 |
| gatgccaatg acaatagttt cagggtgatt gttcccaaga cgttcgacgt gggaacacct | 2340 |
| ggcatcaaaa ataactga | 2358 |

<210> SEQ ID NO 4
<211> LENGTH: 1455
<212> TYPE: DNA
<213> ORGANISM: Falsirhodobacter sp. alg1

<400> SEQUENCE: 4

| | |
|---|---:|
| atgagtctga agctacgcac gttctgtttg gcaggtacgg cgactatttt tgtcgcatta | 60 |
| ccatcaacct atgcattggc agccggaacc ggcgcatgca ccggggtgtc ccagctggcc | 120 |
| attgtatcgg ccagcgatga cggcactttc gatgacatct acgcacctga attcgcgatc | 180 |
| gacggcgaat tcggcccaag ttcgcgctgg tcatcccttg ggagggggaa gcagcttgtt | 240 |
| ctggatctgg gagagcccca gaccgtaagc gaggttggtc tggcctggta caagggcaat | 300 |
| gagcgcacat ccagctttac gctggaagct tcgaatgacg gcgaaaactg gatgcctttg | 360 |
| atggaccgca cggaaagtgc cggaaaatcc gaggctgtgg agaaatacag ctttgacgcg | 420 |
| accgaggccc gctatgttcg ggtgaccggt atgggcaata gcgcgagcgg ctggaacagc | 480 |
| ctttacgagg cacaggtgtt cggctgtggc tcaggtgaga ttgcggccac aggcgacggt | 540 |
| tccggagagg tcaaggaagc agacgtcagc gcctatggcc tgcgtaccga cgttccgcca | 600 |
| agcgagaact tcgatctgac ccactggaag ctgacattgc cggcggatcg ggacaatgac | 660 |
| ggcaaagtgg acgagattga ggaagaagag ctgcagggtt ggtctgatcc ccggttcttc | 720 |
| tataccgatc cggcaacggg tggcatggtt ttccgcaccg ctccggatgg aaagaccacc | 780 |
| tcgggatcgc attatacgcg cagcgaactg cgcgagatga tccgcggcgg tgacaagagc | 840 |
| attgccacgc gcgtggatga cggaacgccc aacaagaaca actgggtgtt ctcgacggcg | 900 |
| cccgaagagg cgcaggccct tgccggcggg gtggacggga ccatgacggc cacgttggcg | 960 |
| gtgaaccatg tgacccgtac cggagaatcc ggcaagatcg gcgtgtcat catcggccag | 1020 |
| atccacgcga tggatgacga gcctatccgg ctttattatc gcaagcttcc gaccaataaa | 1080 |
| tacggctcca tctatttcgc gcatgagccg gtaggggcg acgatgatct ggtcaacgtc | 1140 |
| atcggggatc gtggaagcga tattgacaac cctgcggatg catcgcgct ggacgaagtg | 1200 |
| ttctcttacg agatcaaggt gacatccgaa gaaaaggatg gagagctgca tccgattctg | 1260 |
| aatgttttcca tcacgcgcga tgacggaacg tggtgaaag ccgaacccta cgacatgttc | 1320 |
| gaaagcgggt attcgaccga caaggacttc atgtacttca aggccggagc ctattcgcag | 1380 |
| aacaattcca tcacatggcc ggacgatttc gatcaggtga ccttctacgc gctggatgtg | 1440 | acgcacggcg aataa                                                    1455

<210> SEQ ID NO 5
<211> LENGTH: 36
<212> TYPE: DNA
<213> ORGANISM: Artificial
<220> FEATURE:
<223> OTHER INFORMATION: Exo.Al.Ly_Nde1_F

<400> SEQUENCE: 5
tatcattgca tatgatgtcg acggaaaaca aatccc                             36

<210> SEQ ID NO 6
<211> LENGTH: 27
<212> TYPE: DNA
<213> ORGANISM: Artificial
<220> FEATURE:
<223> OTHER INFORMATION: Exo.Al.Ly_Xho1_R

<400> SEQUENCE: 6
gcagctcgag gttattttg atgccag                                        27

<210> SEQ ID NO 7
<211> LENGTH: 8
<212> TYPE: PRT
<213> ORGANISM: Artificial
<220> FEATURE:
<223> OTHER INFORMATION: HisTag-1

<400> SEQUENCE: 7

Leu Glu His His His His His His
1               5

<210> SEQ ID NO 8
<211> LENGTH: 2379
<212> TYPE: DNA
<213> ORGANISM: Artificial
<220> FEATURE:
<223> OTHER INFORMATION: Fal_sp_alg1+HisTag-1

<400> SEQUENCE: 8
atgtcgacgg aaaacaaatc ccgttcaaac ctgtttccac ttgatgagcc caaagcggga    60
cggctgacga tccaatatgg cccgctcgaa acgacgacgc tgattgaaaa cccgccacgc   120
ttctcatggc tgccggtcat cgaggatggc gcaacctatg cgctgcgcat ctcgaccgat   180
cccgaatatt ccgcggcaaa caccctcctg ttttcgggca tccagctgaa cttcttcacg   240
cctgatgcac ctttggcggc aggcacttgg tactggtcct atgcacaatg cgatgcctcg   300
ggaaagcccg ttaccgaatg gagcacgagc cgtcgcatca ctctcgacga gggtctgcca   360
cagacaccgc tggcaccacg caagacgcgt tttgacgcgg cgaccgtgc gcacccgcgc   420 ctgtggatgg acggcggccg gctggaacag ttccgcaagg atgttgccgc cgacccgacg   480
cattgcacat ggtctacctt tttcgagggt tcggttctgc cgtggatgga ccgcgacatc   540
atcgaagagc ctgtgggcta tccggatcac aagcgtgtcg cgaagatctg gcgcaaggtc   600
tacatcgagt gtcaggaact gatgtatgcg atccgccacc ttgctgtggg cggtcaggtt   660
acccaggacg cggcaatgct ggcacgcgcc aaggaatggc tgctcagcgc cgcacgctgg   720
aatccggcag gcaccaccte gcgcgcctat accgatgaat gggctttccg tgtgaacctc   780
gcactcgcat ggggttatga ctggctctat gaccagctgg acgaggatga gcgtacgctg   840
gtccgcaccg ccttgctgga gcgtacgcgc cagacggcgg atcacctgat gcgccacgcc   900

```
agcatccacc tgtttccgtt tgacagccac gctgtccgcg cggtgtctgc ggttctgatc    960
cccgcctgta ttgccttgct ggatgatgaa cccgaggccg aggactggct gaactatgcg   1020
gtggaattcc tgttcaccgt ctattcgccg tggggcgatc atgacggtgg ctgggccgag   1080
ggtccgcact actggatgac gggtatggcc tatctgatcg acgcggcaaa cctgctgcgc   1140
ggctggagcg gaatcgacct gtaccaacgc ccgttcttcc agaaaaccgg ggacttcccg   1200
ctttatacca aggcgccgga cacacgtcgg gccacattcg gcgatgatag caccatgggc   1260
gatctgcccg cgatcaaggt cggatataac ctgcgtcaat acgcaggggt gaccggcaac   1320
ggtgcctacc aatggtacta cgacgaaatc ctgcgcacca accccggcac ggaaatggcc   1380
ttctacaact ggggctggtg ggatttccgg tttgacgaaa tgctctaccg cacggacttc   1440
ccgatcgtag aggcagttcc gcccgcggat gaggatgcac tgcgctggtt caagggcatc   1500
ggttgggtcg cgatccagca ccgtatgcag gcaccggacg agcatgttca attcgtgttc   1560
aaatcctctc cctacggctc gatcagccac agccatgggg atcagaacgc gttctgtctg   1620
tcggcattcg gtgaggatct tgcaatccag tccggccatt atgtcgcctt caactcgaca   1680
atgcaccaga actggcgtcg ccagaccctg tcgaagaacg ccatcctgat cgacggaaaa   1740
ggccagtacg ccggcaagga caaggcgatt gccatgcaat cgaccggtaa ggtcaatatt   1800
gccgaggatc gtggcgatca tatcttcctg caggggatg cgaccgaagc ctatcgcaca   1860
ttgtcacccg aggtccgctc ggttgtccgt gatgtgtatt tcgtgaatcg cgaatatttc   1920
gtgatcgtgg atgccatcga tgcggatacg cccgtcagca tcgactggcg tctgcacgcg   1980
aatgctccgt tcaatctggg tgatagcagc ttccgctata ccggtgaaaa ggccggtttc   2040
tatggccaga tcctgtggtc cgaggcgggt cctgccgaac tgacgcagga aaccggcttt   2100
ccggatgtcg atccgagcga aatcgaggga ctgccggtca gcacctgcct gaccgcccgt   2160
ttccccaaat ccacccgtca tcgtatcgcg accttgatcg tcccgtatgc tctggatgcg   2220
ccgcgccgca ttttcagctt ccttgatgat cagggttacg actgcgatct ctatttcacc   2280
gatgccaatg acaatagttt cagggtgatt gttcccaaga cgttcgacgt gggaacacct   2340
ggcatcaaaa ataacctcga gcaccaccac caccaccac                          2379
```